(12) United States Patent
Shibano et al.

(10) Patent No.: US 8,993,708 B2
(45) Date of Patent: Mar. 31, 2015

(54) CARBAZOLE POLYMER

(71) Applicant: Nissan Chemical Industries, Ltd., Tokyo (JP)

(72) Inventors: Yuki Shibano, Funabashi (JP); Takuji Yoshimoto, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 14/373,775

(22) PCT Filed: Jan. 22, 2013

(86) PCT No.: PCT/JP2013/051117
§ 371 (c)(1),
(2) Date: Jul. 22, 2014

(87) PCT Pub. No.: WO2013/111713
PCT Pub. Date: Aug. 1, 2013

(65) Prior Publication Data
US 2014/0371421 A1    Dec. 18, 2014

(30) Foreign Application Priority Data

Jan. 23, 2012  (JP) ................. 2012-010699

(51) Int. Cl.
*C08G 59/40* (2006.01)
*H01M 4/60* (2006.01)
*C08G 61/12* (2006.01)

(52) U.S. Cl.
CPC ............. *H01M 4/608* (2013.01); *C08G 61/124* (2013.01); *C08G 61/128* (2013.01)
USPC ........... 528/117; 528/270; 528/423; 524/317; 524/597; 524/609; 524/612; 257/E21.24; 257/E21.219; 438/703; 438/781

(58) Field of Classification Search
USPC .......... 528/117, 270, 423; 524/317, 597, 609, 524/612; 257/E21.219, E21.24; 438/703, 438/781
See application file for complete search history.

(56) References Cited

U.S. PATENT DOCUMENTS

| | | |
|---|---|---|
| 7,282,298 B2 | 10/2007 | Inatomi et al. |
| 8,034,484 B2 | 10/2011 | Inatomi et al. |
| 2012/0077345 A1 | 3/2012 | Saito et al. |

FOREIGN PATENT DOCUMENTS

DE    1145619    *  6/1998    ............. C08G 61/02

(Continued)

OTHER PUBLICATIONS

International Search Report for PCT/JP2013/051117 mailed on May 7, 2013.

(Continued)

*Primary Examiner* — Shane Fang
(74) *Attorney, Agent, or Firm* — Birch, Stewart, Kolasch & Birch, LLP

(57) ABSTRACT

A carbazole polymer including a repeating unit represented by Formula 1 and having excellent one electron oxidation-state stability,

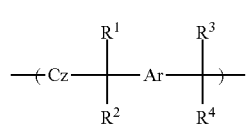

wherein, in Formula 1, $R^1$-$R^4$ each independently represents an alkyl group having 1-60 carbon atoms, a haloalkyl group having 1-60 carbon atoms, or similar, Cz represents a divalent group including a carbazole skeleton represented by Formula 2, and Ar represents a divalent aromatic ring or similar;

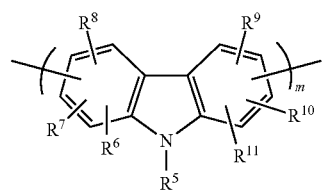

wherein, in Formula 2, $R^5$ represents a hydrogen atom, an alkyl group having 1-60 carbon atoms, or similar, $R^6$-$R^{11}$ each independently represents a hydrogen atom, a halogen atom, or similar, and m represents an integer 1-10.

22 Claims, 10 Drawing Sheets

(56) References Cited

FOREIGN PATENT DOCUMENTS

| JP | 2002-241455 A | 8/2002 |
|---|---|---|
| JP | 4467926 B2 | 5/2010 |
| JP | 4468058 B2 | 5/2010 |
| WO | WO 2010/147155 A1 | 12/2010 |

OTHER PUBLICATIONS

Nakahara et al., "Rechargeable batteries with organic radical cathodes", Chemical Physics Letters, vol. 359, Jun. 27, 2002, pp. 351-354.

Novak et al., "Electrochemically Active Polymers for Rechargeable Batteries", Chem. Rev., vol. 97, 1997, pp. 207-281.

Saeed et al., "Novel carbazole-pyridine copolymers by an economical method: synthesis, spectroscopic and thermochemical studies", Beilstein Journal of Organic Chemistry, vol. 7, 2011, pp. 638-647.

Tran-Van et al., "Synthesis and electrochemical properties of mixed ionic and electronic modified polycarbazole", Electrochimica Acta, vol. 47, 2002, pp. 2927-2936.

Written Opinion of the International Searching Authority for PCT/JP2013/051117 mailed on May 7, 2013.

* cited by examiner

CARBAZOLE POLYMER

TECHNICAL FIELD

The present invention relates to a carbazole polymer. More particularly, the invention relates to a carbazole polymer having a stable oxidation state.

BACKGROUND ART

Over the past few years, extensive research has been carried out on enhancing the performance of lithium ion secondary batteries, the aim being to increase energy density and safety. In particular, given that the active material serving as the electrical energy-storing core has a direct bearing on enhanced performance in lithium ion secondary batteries, intensive research and development is being conducted on materials which, in terms of electrical capacity and other characteristics, are superior to the lithium cobaltate in current use. For example, research is being carried out on inorganic solid active materials such as cobalt-nickel-manganese ternary oxides having higher capacities and energy densities than lithium cobaltate, and olivine-type phosphates that exhibit extremely stable redox behaviors.

At the same time, a number of attempts are being made to use organic substances as active materials. Resources for organic active materials are more abundant than those for existing inorganic layered compounds, and there is a possibility that higher capacity can be achieved by molecular design. For example, among low-molecular-weight π-conjugated compounds such as those mentioned in Patent Documents 1 and 2 are several which exhibit a stable redox behavior involving two or more electrons and whose use as positive electrode materials for lithium ion secondary batteries is being investigated.

However, because low-molecular-weight materials undergo large changes in polarity when electron transfer is carried out, dissolution of these materials in the electrolyte solution readily arises, as a result of which the cycle performance is often low. Also, because these materials lack electrical conductivity, it is necessary to use a large amount of conductive additive in order to lower the internal resistance of the battery. As a result, even if the low-molecular-weight material itself has a large capacity, the capacity of the overall electrode ends up being a small value.

By contrast, main chain-conjugated polymers are materials which can be reversibly oxidized and reduced. Given also the advantage that, as polymers, dissolution in the electrolyte solution can be suppressed, as mentioned in Non-Patent Document 1, practical research is being carried out on the use of such polymers as positive electrode active materials for lithium ion secondary batteries.

However, main chain-conjugated polymers have the drawback that, as oxidation proceeds, electrostatic repulsions between oxidants (radical cations) on the main chain increase, as a result of which the capacity does not reach the theoretical capacity calculated from the structure and ends up being relatively low.

From this perspective, a number of development efforts are being carried out on the use of, as electrode active materials, polymeric compounds which have electrochemically active sites in a non-conjugated form such as that mentioned in Non-Patent Document 2. However, carbazole-containing polymers with a stable oxidation state have not hitherto been employed.

PRIOR ART DOCUMENTS

Patent Documents

Patent Document 1: JP No. 4467926
Patent Document 2: JP No. 4468058

Non-Patent Documents

Non-Patent Document 1: Chem. Rev., 97, 207 (1997)
Non-Patent Document 2: Chem. Phys. Lett., 359, 351 (2002)

SUMMARY OF THE INVENTION

Problems to be Solved by the Invention

In light of such circumstances, an object of this invention is to provide a carbazole polymer having a stable oxidation state.

Means for Solving the Problems

The inventors have conducted extensive investigations, as a result of which they have discovered that polymers formed by bonding carbazole with linkers that include specific structures have a one-electron oxidation state of excellent stability.

Accordingly, the invention provides:
1. A carbazole polymer characterized by including recurring units of formula (1)

[Chemical Formula 1]

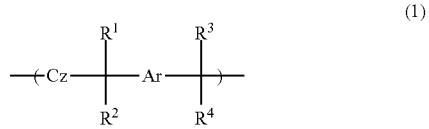

(in formula (1), $R^1$ to $R^4$ are each independently an alkyl group of 1 to 60 carbons, a haloalkyl group of 1 to 60 carbons, a cycloalkyl group of 3 to 60 carbons, a bicycloalkyl group of 4 to 60 carbons, an alkenyl group of 2 to 60 carbons, an alkynyl group of 2 to 60 carbons, an aromatic group of 6 to 60 carbons or a heteroaromatic group of 2 to 60 carbons (which alkyl, haloalkyl, cycloalkyl, bicycloalkyl, alkenyl, alkynyl, aromatic and heteroaromatic groups may be substituted with Z); Cz is a divalent group that includes the carbazole skeleton of formula (2)

[Chemical Formula 2]

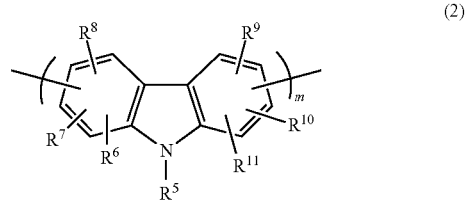

(in formula (2), $R^5$ being a hydrogen atom, an alkyl group of 1 to 60 carbons, a haloalkyl group of 1 to 60 carbons, a cycloalkyl group of 3 to 60 carbons, a bicycloalkyl group of 4 to 60 carbons, an alkenyl group of 2 to 60 carbons, an alkynyl group of 2 to 60 carbons, an aromatic group of 6 to 60 carbons or a heteroaromatic group of 2 to 60 carbons (which alkyl, haloalkyl, cycloalkyl, bicycloalkyl, alkenyl, alkynyl, aromatic and heteroaromatic groups may be substituted with Z, and which alkyl groups and haloalkyl groups may include an ether structure), $R^6$ to $R^{11}$ being each independently a hydrogen atom, a halogen atom, a nitro group, a cyano group, an amino group, a hydroxyl group, a thiol group, a phosphate group, a sulfonic acid group, a carboxyl group, an alkoxy group of 1 to 60 carbons, a thioalkoxy group of 1 to 60 carbons, an alkyl group of 1 to 60 carbons, a haloalkyl group of 1 to 60 carbons, a cycloalkyl group of 3 to 60 carbons, a bicycloalkyl group of 4 to 60 carbons, an alkenyl group of 2 to 60 carbons, an alkynyl group of 2 to 60 carbons, an acyl group of 1 to 60 carbons, an aromatic group of 6 to 60 carbons or a heteroaromatic group of 2 to 60 carbons (which alkoxy, thioalkoxy, alkyl, haloalkyl, cycloalkyl, bicycloalkyl, alkenyl, alkynyl, acyl, aromatic and heteroaromatic groups may be substituted with Z), and m being an integer from 1 to 10); Ar is a divalent aromatic ring or heteroaromatic ring (which aromatic and heteroaromatic rings may be substituted with Z); and Z is a halogen atom, a nitro group, a cyano group, an amino group, a hydroxyl group, a thiol group, a phosphate group, a sulfonic acid group, a carboxyl group, an alkoxy group of 1 to 60 carbons, a thioalkoxy group of 1 to 60 carbons, an alkyl group of 1 to 60 carbons, a haloalkyl group of 1 to 60 carbons, a cycloalkyl group of 3 to 60 carbons, a bicycloalkyl group of 4 to 60 carbons, an alkenyl group of 2 to 60 carbons, an alkynyl group of 2 to 60 carbons, an acyl group of 1 to 60 carbons, an aromatic group of 6 to 60 carbons or a heteroaromatic group of 2 to 60 carbons);

2. The carbazole polymer according to 1 above, wherein Cz is a divalent group containing a carbazole skeleton of formula (3)

[Chemical Formula 3]

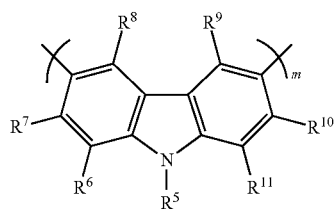

(3)

(wherein $R^5$ to $R^{11}$ and m are as defined above);

3. The carbazole polymer according to 1 or 2 above, wherein $R^1$ to $R^4$ are each independently an alkyl group of 1 to 10 carbons or a haloalkyl group of 1 to 10 carbons;

4. The carbazole polymer according to 3 above, wherein $R^1$ to $R^4$ are each independently an alkyl group of 1 to 10 carbons;

5. The carbazole polymer according to any of 1 to 4 above, wherein $R^5$ is a hydrogen atom, an alkyl group of 1 to 10 carbons, a haloalkyl group of 1 to 10 carbons or a group of formula (4)

[Chemical Formula 4]

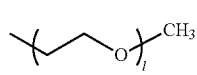

(4)

(wherein l is an integer from 1 to 10);

6. The carbazole polymer according to 5 above, wherein $R^5$ is an alkyl group of 1 to 10 carbons or a group of formula (4')

[Chemical Formula 5]

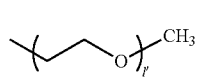

(4')

(wherein l' is an integer from 1 to 5);

7. The carbazole polymer according to any of 1 to 6 above, wherein $R^6$ to $R^{11}$ are each independently a hydrogen atom, a halogen atom, an alkyl group of 1 to 10 carbons, a haloalkyl group of 1 to 10 carbons or an alkoxy group of 1 to 10 carbons;

8. The carbazole polymer according to any of 1 to 7 above, wherein Ar is a divalent aromatic ring of any of formulas (5) to (7)

[Chemical Formula 6]

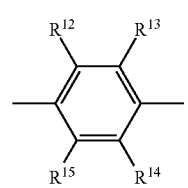

(5)

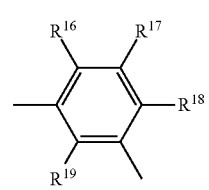

(6)

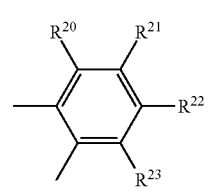

(7)

(in formulas (5) to (7), $R^{12}$ to $R^{23}$ are each independently a hydrogen atom, a halogen atom, an alkyl group of 1 to 10 carbons, a haloalkyl group of 1 to 10 carbons or an alkoxy group of 1 to 10 carbons);

9. The carbazole polymer according to any of 1 to 8 above, wherein m is an integer from 1 to 3;

10. The carbazole polymer according to any of 1 to 9 above of formula (8) or (9)

[Chemical Formula 7]

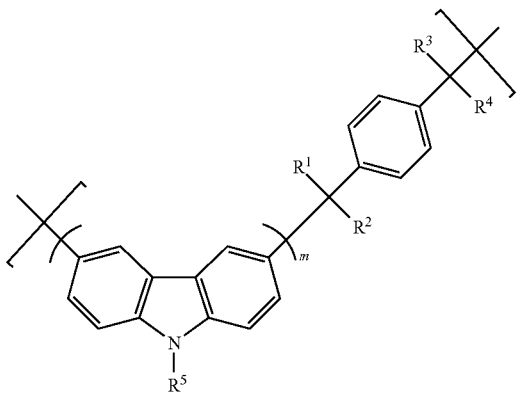

(8)

-continued (9)

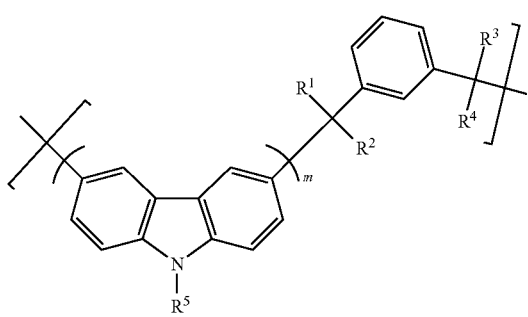

(wherein $R^1$ to $R^5$ and m are as defined above);

11. A method of synthesizing the carbazole polymer according to 1 above, the method being characterized by reacting a carbazole derivative of formula (10) and a bisalcohol compound of formula (11) in the presence of an acid catalyst

[Chemical Formula 8]

(10)

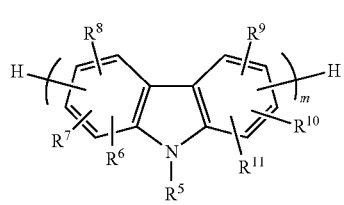

(11)

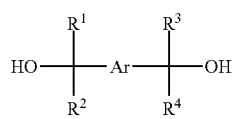

(wherein $R^1$ to $R^{11}$, Ar and m are as defined above);

12. The method according to 11 above, wherein the carbazole derivative has formula (12)

[Chemical Formula 9]

(12)

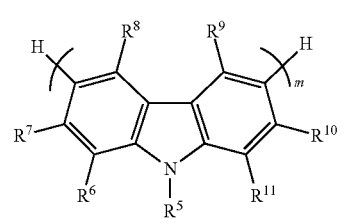

(wherein $R^5$ to $R^{11}$ are as defined above);

13. The method according to 11 or 12 above, wherein $R^6$ to $R^{11}$ are each independently a hydrogen atom, a halogen atom, an alkyl group of 1 to 10 carbons, a haloalkyl group of 1 to 10 carbons or an alkoxy group of 1 to 10 carbons;

14. The method according to any of 11 to 13 above, wherein $R^5$ is a hydrogen atom, an alkyl group of 1 to 10 carbons, a haloalkyl group of 1 to 10 carbons or a group of formula (4)

[Chemical Formula 10]

(4)

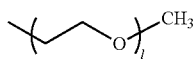

(wherein l is an integer from 1 to 10);

15. The method according to any of 11 to 14 above, wherein Ar is a divalent aromatic ring of any of formulas (5) to (7)

[Chemical Formula 11]

(5)

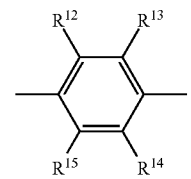

(6)

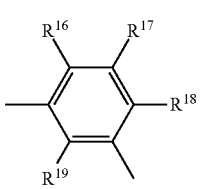

(7)

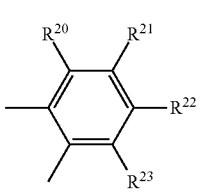

(in formulas (5) to (7), $R^{12}$ to $R^{23}$ are each independently a hydrogen atom, a halogen atom, an alkyl group of 1 to 10 carbons, a haloalkyl group of 1 to 10 carbons or an alkoxy group of 1 to 10 carbons);

16. The method according to any of 11 to 15 above, wherein m is an integer from 1 to 3;

17. An electrode active material which includes the carbazole polymer according to any of 1 to 10 above;

18. A composition which includes the carbazole polymer according to any of 1 to 10 above;

19. The composition according to 18 above which is adapted for use in a secondary battery electrode;

20. An organic electrical storage device which uses the carbazole polymer according to any of 1 to 10 above;

21. An electrode which includes the electrode active material according to 17 above; and 22. A secondary battery which includes the electrode according to 21 above.

Advantageous Effects of the Invention

This invention is able to provide a carbazole polymer having a one-electron oxidation state with a high stability.

Although the reason why the carbazole polymer of this invention has an excellent oxidation state stability is not entirely clear, it appears as if the fact that the carbon atoms bonded to the carbazole skeleton are quaternary carbons is related to the high stability.

That is, as shown in the reaction schemes below, when a hydrogen atom is present on a carbon atom bonded to carbazole, because the radical cation that has formed owing to oxidation of the carbazole site stabilizes due to extension of the conjugated system, it is thought that the molecular structure changes with the elimination of a hydrogen radical. On the other hand, if the carbon atom bonded to carbazole is a quaternary carbon, because no hydrogen atoms are present, the above elimination does not take place and so the carbazole is thought to exist stably as a radical cation.

Because the carbazole polymer of the invention has a one-electron oxidation state with a high stability, it can be advantageously used as the active material in a lithium ion battery. Use of the inventive carbazole polymer as an active material in secondary batteries other than lithium ion batteries (e.g., sodium ion secondary batteries) and lithium ion capacitors also appears to be promising.

[Chemical Formula 12]

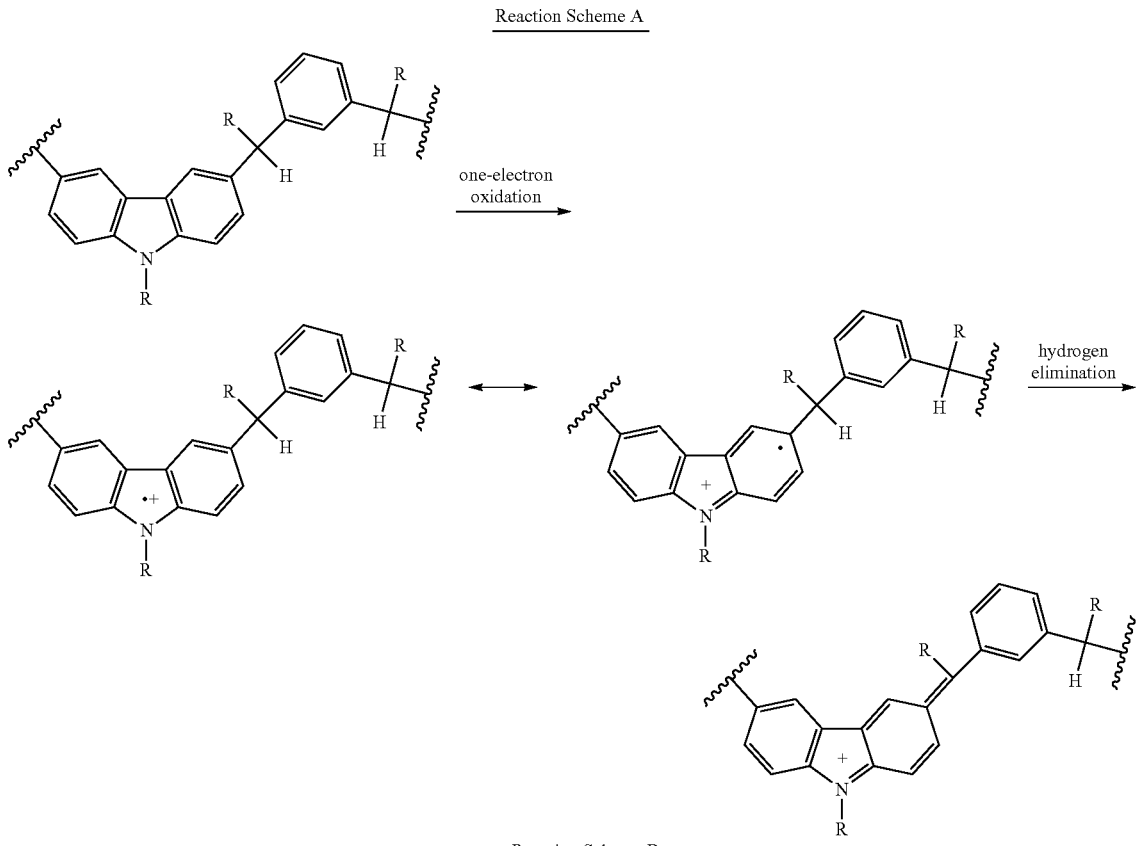

BRIEF DESCRIPTION OF THE DIAGRAMS

EMBODIMENT FOR CARRYING OUT THE INVENTION

Figure 1:
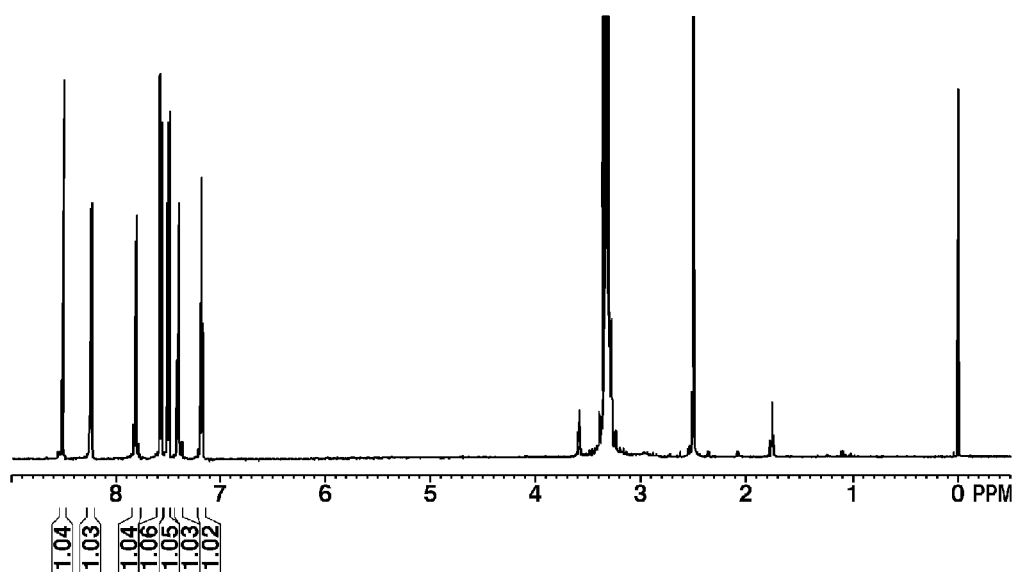
FIG. 1 is an $^1$H-NMR spectrum of the (Cz)$_2$ prepared in Synthesis Example 1.

The invention is described more fully below.

The carbazole polymer according to the invention includes recurring units of above formula (1).

As mentioned above, in the carbazole polymer of the invention, to achieve a high oxidation state stability, it is essential for the carbon atoms bonded to the carbazole to be quaternary carbons. In formula (1), none of $R^1$ to $R^4$ are hydrogen atoms; these are each independently an alkyl group of 1 to 60 carbons, a haloalkyl group of 1 to 60 carbons, a cycloalkyl group of 3 to 60 carbons, a bicycloalkyl group of 4 to 60 carbons, an alkenyl group of 2 to 60 carbons, an alkynyl group of 2 to 60 carbons, an aromatic group of 6 to 60 carbons or a heteroaromatic group of 2 to 60 carbons.

Illustrative examples of alkyl groups of 1 to 60 carbons, which may be linear or branched, include methyl, ethyl, n-propyl, i-propyl, n-butyl, i-butyl, s-butyl, t-butyl, n-pentyl, 1-methyl-n-butyl, 2-methyl-n-butyl, 3-methyl-n-butyl, 1,1-dimethyl-n-propyl, n-hexyl, 1-methyl-n-pentyl, 2-methyl-n-pentyl, 1,1-dimethyl-n-butyl, 1-ethyl-n-butyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-heneicosyl, n-docosyl, n-tricosyl, n-tetracosyl, n-pentacosyl, n-hexacosyl, n-heptacosyl, n-octacosyl, n-nonacosyl and n-triacontyl.

Haloalkyl groups of 1 to 60 carbons are exemplified by the above alkyl groups of 1 to 60 carbons in which at least one hydrogen atom is substituted with a halogen atom. Examples of the halogen atoms include fluorine, chlorine, bromine and iodine.

Illustrative examples of such haloalkyl groups include monofluoromethyl, difluoromethyl, trifluoromethyl, bromodifluoromethyl, 2-chloroethyl, 2-bromoethyl, 1,1-difluoroethyl, 2,2,2-trifluoroethyl, 1,1,2,2-tetrafluoroethyl, 2-chloro-1,1,2-trifluoroethyl, pentafluoroethyl, 3-bromopropyl, 2,2,3,3-tetrafluoropropyl, 1,1,2,3,3,3-hexafluoropropyl, 1,1,1,3,3,3-hexafluoropropan-2-yl, 3-bromo-2-methylpropyl, 4-bromobutyl and perfluoropentyl.

Illustrative examples of cycloalkyl groups of 3 to 60 carbons include cyclopropyl, cyclobutyl, cyclopentyl, cyclohexyl, cycloheptyl, cyclooctyl, cyclononyl, cyclodecyl and cycloundecyl.

Illustrative examples of bicycloalkyl groups of 4 to 60 carbons include bicyclobutyl, bicyclopentyl, bicyclohexyl, bicycloheptyl, bicyclooctyl, bicyclononyl and bicyclodecyl.

Illustrative examples of alkenyl groups of 2 to 60 carbons, which may be linear or branched, include ethenyl, n-1-propenyl, n-2-propenyl, 1-methylethenyl, n-1-butenyl, n-2-butenyl, n-3-butenyl, 2-methyl-1-propenyl, 2-methyl-2-propenyl, 1-ethylethenyl, 1-methyl-1-propenyl, 1-methyl-2-propenyl, n-1-pentenyl, n-2-pentenyl, n-3-pentenyl, n-4-pentenyl, 1-n-propylethenyl, 1-methyl-1-butenyl, 1-methyl-2-butenyl, 1-methyl-3-butenyl, 2-ethyl-2-propenyl, 2-methyl-1-butenyl, 2-methyl-2-butenyl, 2-methyl-3-butenyl, 3-methyl-1-butenyl, 3-methyl-2-butenyl, 3-methyl-3-butenyl, 1,1-dimethyl-2-propenyl, 1-i-propylethenyl, 1,2-dimethyl-1-propenyl, 1,2-dimethyl-2-propenyl, n-1-hexenyl, n-2-hexenyl, n-3-hexenyl, n-4-hexenyl, n-5-hexenyl, n-heptenyl, n-octenyl, n-nonenyl, n-decenyl, n-undecenyl, n-dodecenyl, n-tetradecenyl, n-pentadecenyl, n-hexadecenyl, n-heptadecenyl, n-octadecenyl, n-nonadecenyl, n-eicosenyl, n-heneicosenyl, n-docosenyl, n-tricosenyl, n-tetracosenyl, n-pentacosenyl, n-hexacosenyl, n-heptacosenyl, n-octacosenyl, n-nonacosenyl and n-triacontenyl.

Illustrative examples of alkynyl groups of 2 to 60 carbons, which may be linear or branched, include ethynyl, n-1-propynyl, n-2-propynyl, n-1-butynyl, n-2-butynyl, n-3-butynyl, 1-methyl-2-propynyl, n-1-pentynyl, n-2-pentynyl, n-3-pentynyl, n-4-pentynyl, 1-methyl-n-butynyl, 2-methyl-n-butynyl, 3-methyl-n-butynyl, 1,1-dimethyl-n-propynyl, n-1-hexynyl, n-2-hexynyl, n-3-hexynyl, n-4-hexynyl, n-5-hexynyl, 1-methyl-n-pentynyl, 2-methyl-n-pentynyl, 1,1-dimethyl-n-butynyl, 1-ethyl-n-butynyl, 1,1,2-trimethyl-n-propynyl, n-heptynyl, n-octynyl, n-nonynyl, n-decynyl, n-undecynyl, n-dodecynyl, n-tridecynyl, n-tetradecynyl, n-pentadecynyl, n-hexadecynyl, n-heptadecynyl, n-octadecynyl, n-nonadecynyl and n-eicosynyl.

Illustrative examples of aromatic groups of 6 to 60 carbons include phenyl, α-naphthyl, β-naphthyl, o-biphenylyl, m-biphenylyl, p-biphenylyl, anthracenyl, phenanthryl, fluorenyl, p-terphenyl, m-terphenyl, tetracenyl, pentacenyl and perylenyl.

Illustrative examples of heteroaromatic groups of 2 to 60 carbons include 2- and 3-thienyl, 2- and 3-furyl, 2-, 4- and 5-oxazolyl, 2-, 4- and 5-thiazolyl, 2- and 4-imidazolyl, 2-, 3- and 4-pyridyl, 2-, 4- and 5-pyrimidinyl, 2-pyrazinyl, 3- and 4-pyridazinyl, 2- and 3-pyrazyl, 2-, 3-, 4-, 5-, 6-, 7- and 8-quinolyl, 2-, 5- and 6-quinoxalyl, 2-, 4-, 5-, b- and 7-benzoxazolyl, 2-, 4-, 5-, 6- and 7-benzothiazolyl, and 2-, 4- and 5-benzoimidazolyl.

In each of these alkyl, haloalkyl, cycloalkyl, bicycloalkyl, alkenyl, alkynyl, aromatic and heteroaromatic groups, one or more hydrogen atom may be substituted with a substituent Z, such as a halogen atom, a nitro group, a cyano group, an amino group, a hydroxyl group, a thiol group, a phosphate group, a sulfonic acid group, a carboxyl group, an alkoxy group of 1 to 60 carbons, a thioalkoxy group of 1 to 60 carbons, an alkyl group of 1 to 60 carbons, a haloalkyl group of 1 to 60 carbons, a cycloalkyl group of 3 to 60 carbons, a bicycloalkyl group of 4 to 60 carbons, an alkenyl group of 2 to 60 carbons, an alkynyl group of 2 to 60 carbons, an acyl group of 1 to 60 carbons, an aromatic group of 6 to 60 carbons or a heteroaromatic group of 2 to 60 carbons.

Illustrative examples of alkoxy groups of 1 to 60 carbons, in which the alkyl group may be linear, branched or cyclic, include methoxy, ethoxy, n-propoxy, i-propoxy, c-propoxy, n-butoxy, i-butoxy, s-butoxy, t-butoxy, c-butoxy, n-pentoxy, c-pentoxy, n-hexoxy, c-hexoxy, n-heptyloxy, n-octyloxy, n-nonyloxy, n-decyloxy, n-undecyloxy, n-dodecyloxy, n-tridecyloxy, n-tetradecyloxy, n-pentadecyloxy, n-hexadecyloxy, n-heptadecyloxy, n-octadecyloxy, n-nonadecyloxy, n-eicosyloxy, n-heneicosyloxy, n-docosyloxy, n-tricosyloxy, n-tetracosyloxy, n-pentacosyloxy, n-hexacosyloxy, n-heptacosyloxy, n-octacosyloxy, n-nonacosyloxy and n-triacontyloxy.

Illustrative examples of thioalkoxy groups of 1 to 60 carbons include groups in which the oxygen atom in the above alkoxy groups is substituted with a sulfur atom.

Illustrative examples of acyl groups of 1 to 60 carbons include formyl, acetyl, propionyl, butyryl, i-butyryl, valeryl, i-valeryl, pivaroyl, caproyl, enanthyl, caprylyl, pelargonyl and capryl.

In addition, the foregoing halogen atoms, alkyl groups, haloalkyl groups, cycloalkyl groups, bicycloalkyl groups, alkenyl groups, alkynyl groups, aromatic groups and heteroaromatic groups are exemplified by the same groups as mentioned above.

Among these, from the standpoint of further increasing the solubility of the resulting carbazole polymer, $R^1$ to $R^4$ are preferably alkyl groups of 1 to 10 carbons or haloalkyl groups of 1 to 10 carbons, and more preferably alkyl groups of 1 to 10 carbons. Linear alkyl groups of 1 to 10 carbons, such as methyl, ethyl, n-propyl, n-butyl and n-pentyl, are especially preferred.

In formula (1), Cz is a divalent group containing a carbazole skeleton of above formula (2).

In formula (2), $R^5$ is a hydrogen atom, an alkyl group of 1 to 60 carbons, a haloalkyl group of 1 to 60 carbons, a cycloalkyl group of 3 to 60 carbons, a bicycloalkyl group of 4 to 60 carbons, an alkenyl group of 2 to 60 carbons, an alkynyl group of 2 to 60 carbons, an aromatic group of 6 to 60 carbons, or a heteroaromatic group of 2 to 60 carbons. These respective groups are exemplified by the same groups as those mentioned above with reference to $R^1$ to $R^4$.

One or more of the hydrogen atoms in these alkyl groups, haloalkyl groups, cycloalkyl groups, bicycloalkyl groups, alkenyl groups, alkynyl groups, aromatic groups and heteroaromatic groups may be substituted with the above-described substituent Z. Moreover, the alkyl groups, haloalkyl groups, cycloalkyl groups, bicycloalkyl groups, alkenyl groups and alkynyl groups may contain an ether structure.

In this invention, illustrative examples of such alkyl groups containing an ether bond include $CH_2OCH_3$, $CH_2OCH_2CH_3$, $CH_2O(CH_2)_2CH_3$, $CH_2OCH(CH_3)_2$, $CH_2O(CH_2)_3CH_3$, $CH_2OCH_2CH(CH_3)_2$, $CH_2OCH(CH_3)_3$, $CH_2O(CH_2)_4CH_3$, $CH_2OCH(CH_3)(CH_2)_2CH_3$, $CH_2O(CH_2)_2CH(CH_3)_3$, $CH_2OCH(CH_3)(CH_2)_3CH_3$, $CH_2O(CH_2)_5CH_3$, $CH_2OCH_2CH(CH_3)(CH_2)_2CH_3$, $CH_2O(CH_2)_2CH(CH_3)$ $CH_2CH_3$, $CH_2O(CH_2)_3CH(CH_3)_2$, $CH_2OC(CH_3)_2$ $(CH_2)_2CH_3$, $CH_2OCH(CH_2CH_3)(CH_2)_2CH_3$, $CH_2OC$ $(CH_3)_2CH(CH_3)_2$, $CH_2O(CH_2)_6CH_3$, $CH_2O(CH_2)_7CH_3$, $CH_2OCH_2CH(CH_2CH_3)(CH_2)_3CH_3$, $CH_2O(CH_2)_8CH_3$, $CH_2O(CH_2)_9CH_3$, $CH_2O(CH_2)_{10}CH_3$, $CH_2O(CH_2)_{11}CH_3$, $CH_2O(CH_2)_{12}CH_3$, $CH_2O(CH_2)_{13}CH_3$, $CH_2O(CH_2)_{14}CH_3$, $CH_2O(CH_2)_{15}CH_3$, $CH_2O(CH_2)_{16}CH_3$, $CH_2O(CH_2)_{17}CH_3$, $CH_2O(CH_2)_{18}CH_3$, $CH_2CH_2OCH_3$, $CH_2CH_2OCH_2CH_3$, $CH_2CH_2O(CH_2)_2CH_3$, $CH_2CH_2OCH(CH_3)_3$, $CH_2CH_2O$ $(CH_2)_3CH_3$, $CH_2CH_2OCH_2CH(CH_3)_2$, $CH_2CH_2OC$ $(CH_3)_3CH_2CH_2O(CH_2)_4CH_3$, $CH_2CH_2OCH(CH_3)$ $(CH_2)_2CH_3$, $CH_2CH_2OCH_2CH(CH_3)_3$, $CH_2CH_2O$ $(CH_2)_2CH(CH_3)_2$, $CH_2CH_2OC(CH_3)_3$, $CH_2CH_2OCH(CH_3)$ $(CH_2)_3CH_3$, $CH_2CH_2O(CH_2)_5CH_3$, $CH_2CH_2OCH(CH_3)$ $(CH_2)_3CH_3$, $CH_2CH_2OCH_2CH(CH_3)(CH_2)_2CH_3$, $CH_2CH_2OCH_2CH(CH_3)_3$, $CH_2CH_2OCH$ $(CH_2CH_3)(CH_2)_2CH_3$, $CH_2CH_2OC(CH_3)_2(CH_2)_2CH_3$, $CH_2CH_2OCH(CH_2CH_3)(CH_2)_2CH_3$, $CH_2CH_2OC$ $(CH_3)_2CH(CH_3)_2$, $CH_2CH_2O(CH_2)_6CH_3$, $CH_2CH_2CH_2O(CH_2)_7CH_3$, $CH_2CH_2CH_2OCH_2CH$ $(CH_2CH_3)(CH_2)_3CH_3$, $CH_2CH_2O(CH_2)_8CH_3$, $CH_2CH_2CH_2O(CH_2)_9CH_3$, $CH_2CH_2O(CH_2)_{10}CH_3$, $CH_2CH_2O(CH_2)_{11}CH_3$, $CH_2CH_2O(CH_2)_{12}CH_3$, $CH_2CH_2O(CH_2)_{13}CH_3$, $CH_2CH_2O(CH_2)_{14}CH_3$, $CH_2CH_2O(CH_2)_{15}CH_3$, $CH_2CH_2O(CH_2)_{16}CH_3$, $CH_2CH_2OCH_2CH_2OCH_3$, $CH_2CH_2OCH_2CH_2OCH_2CH_2OCH_3$, $CH_2CH_2OCH_2CH_2OCH_2CH_2OCH_2CH_2OCH_3$, $CH_2CH_2OCH_2CH_2OCH_2CH_2OCH_2CH_2OCH_2CH_2OCH_3$, $CH_2CH_2OCH_2CH_2OCH_2CH_2OCH_2CH_2OCH_2$ $CH_2OCH_3$, $CH_2CH_2OCH_2CH_2OCH_2CH_2OCH_2$ $CH_2OCH_2CH_2OCH_2CH_2OCH_3$, $CH_2CH_2OCH_2CH_2OCH_2CH_2OCH_2CH_2OCH_2$ $CH_2OCH_2CH_2OCH_2CH_2OCH_3$, $CH_2CH_2CH_2OCH_2CH_2CH_2OCH_3$, $CH_2CH_2CH_2OCH_2CH_2CH_2OCH_2CH_2CH_2OCH_3$, $CH_2CH_2CH_2OCH_2CH_2CH_2OCH_2CH_2CH_2OCH_2CH_2$ $CH_2OCH_3$, $CH_2CH_2CH_2OCH_2CH_2CH_2OCH_2$ $CH_2CH_2OCH_2CH_2CH_2OCH_2CH_2CH_2OCH_3$, $CH_2CH_2CH_2OCH_2CH_2CH_2OCH_2CH_2CH_2OCH_2CH_2CH_2$ $OCH_2CH_2CH_2OCH_2CH_2CH_2OCH_3$, $CH_2CH_2CH_2OCH_2CH_2CH_2OCH_2CH_2CH_2OCH_2CH_2CH_2$ $OCH_3$, $CH_2CH_2CH_2OCH_2CH_2CH_2OCH_2CH_2$ $OCH_3$, $CH_2CH_2OCH_2CH_2CH_2OCH_2CH_2OCH_2CH_2$ $OCH_2CH_2OCH_2CH_3$, $CH_2O(CH_2)_{19}CH_3$, $CH_2CH_2O(CH_2)_{18}CH_3$, $CH_2CH_2O(CH_2)_{19}CH_3$, $CH_2CH_2CH_2O(CH_2)_{17}CH_3$, $CH_2CH_2CH_2O(CH_2)_{18}CH_3$, $CH_2CH_2CH_2O(CH_2)_{19}CH_{13}$, $CH_2CH_2CH_2OCH_2CH_2CH_2OCH_2CH_2CH_2OCH_2CH_2$ $CH_2OCH_2CH_2CH_2OCH_2CH_2CH_2OCH_2CH_2OCH_3$, $CH_2CH_2CH_2OCH_2CH_2CH_2OCH_2CH_2OCH_2CH_2$ $OCH_2CH_2CH_2OCH_2CH_2CH_2OCH_2CH_2CH_2OCH_2$ $CH_2CH_2OCH_3$, $CH_2CH_2CH_2CH_2OCH_2$ $CH_2CH_2CH_2OCH_2CH_2CH_2CH_2OCH_2CH_2CH_2OCH_2$ $CH_2CH_2CH_2OCH$, $CH_2CH_2CH_2CH_2OCH_2$ $CH_2CH_2CH_2OCH_2CH_2CH_2CH_2OCH_2CH_2CH_2CH_2OCH_2$ $CH_2CH_2CH_2CH_2OCH_2CH_2CH_2CH_2OCH_3$, $CH_2CH_2CH_2CH_2OCH_2CH_2CH_2CH_2OCH_2CH_2CH_2CH_2$ $OCH_2CH_2CH_2CH_2OCH_2CH_2CH_2CH_2OCH_2CH_2CH_2$ $CH_2OCH_2CH_2CH_2CH_2OCH_3$, $CH_2CH_2OCH_2CH_2OCH_2CH_3$ and $CH_2CH_2OCH_2CH_2OCH_2CH_2OCH_2CH_3$.

Illustrative examples of haloalkyl groups containing an ether bond include groups in which at least one hydrogen atom in the above alkyl groups is substituted with a halogen atom.

Of these, from the standpoint of further increasing the solubility of the resulting carbazole polymer, $R^5$ is preferably a hydrogen atom, an alkyl group of 1 to 10 carbons, a haloalkyl group of 1 to 10 carbons or a group of formula (4) below, and is more preferably an alkyl group of 1 to 10 carbons or a group of formula (4') below.

[Chemical Formula 13]

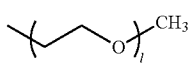
(4)

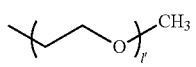
(4')

In the formulas, l is an integer from 1 to 10, and l' is an integer from 1 to 5.

In formula (2), $R^6$ to $R^{11}$ are each independently a hydrogen atom, a halogen atom, a nitro group, a cyano group, an amino group, a hydroxyl group, a thiol group, a phosphate group, a sulfonic acid group, a carboxyl group, an alkoxy group of 1 to 60 carbons, a thioalkoxy group of 1 to 60 carbons, an alkyl group of 1 to 60 carbons, a haloalkyl group of 1 to 60 carbons, a cycloalkyl group of 3 to 60 carbons, a bicycloalkyl group of 4 to 60 carbons, an alkenyl group of 2 to 60 carbons, an alkynyl group of 2 to 60 carbons, an acyl group of 1 to 60 carbons, an aromatic group of 6 to 60 carbons or a heteroaromatic group of 2 to 60 carbons. These groups are exemplified by the same groups as those mentioned above as examples of $R^1$ to $R^4$ and the substituent Z.

One or more hydrogen atom on the above alkoxy group, thioalkoxy group, alkyl group, haloalkyl group, cycloalkyl group, bicycloalkyl group, alkenyl group, alkynyl group, acyl group, aromatic group and heteroaromatic group may be substituted with the above-described substituent Z.

Of these, from the standpoint of achieving a good balance between enhanced stability of the resulting carbazole polymer and the polymerization reactivity of the monomer during polymer synthesis, $R^6$ to $R^{11}$ are preferably hydrogen atoms (achieving a higher molecular weight in the resulting polymer), halogen atoms, alkyl groups of 1 to 10 carbons, haloalkyl groups of 1 to 10 carbons or alkoxy groups of 1 to 10 carbons, and are more preferably hydrogen atoms, linear alkyl groups of 1 to 10 carbons or alkoxy groups containing a linear alkyl group of 1 to 10 carbons.

In formula (2), the letter m is an integer from 1 to 10, and is preferably an integer from 1 to 3.

In above formula (2), quaternary carbon atoms may be substituted at any site on the carbazole skeleton, although the structure of formula (3) below in which a quaternary carbon atom is bonded at each of the p positions with respect to the nitrogen atom on the carbazole ring is preferred.

[Chemical Formula 14]

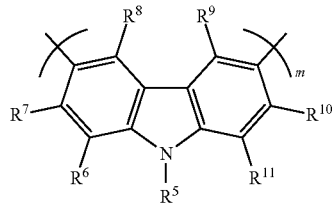
(3)

In the formula, $R^5$ to $R^{11}$ and m are the same as above.

In above formula (1), Ar is a divalent aromatic ring or a heteroaromatic ring.

Illustrative examples of divalent aromatic rings include 1,2-phenylene, 1,3-phenylene, 1,4-phenylene, 1,6-naphthylene, 1,7-naphthylene, 2,6-naphthylene and 2,7-naphthylene groups.

Illustrative examples of divalent heteroaromatic rings include divalent imidazole rings, pyridine rings, pyrimidine rings, indole rings, quinoline rings, furan rings and thiophene rings.

In these aromatic rings and heteroaromatic rings, at least one hydrogen atom may be substituted with the above-described substituent Z.

Of these, Ar is preferably a divalent group of any one of formulas (5) to (7) below, and more preferably a divalent group of formula (5) or (6).

In formulas (5) to (7), $R^{12}$ to $R^{23}$ are each independently a hydrogen atom, a halogen atom, an alkyl group of 1 to 10 carbons, a haloalkyl group of 1 to 10 carbons or an alkoxy group of 1 to 10 carbons. Specific examples of these include the same groups having 1 to 10 carbons from among the alkyl groups, haloalkyl groups and alkoxy groups mentioned above, although hydrogen atoms are especially preferred.

[Chemical Formula 15]

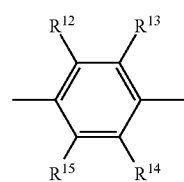
(5)

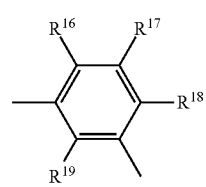
(6)

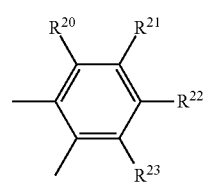
(7)

In this invention, preferred carbazole polymers include, but are not limited to, those of formulas (8) or (9) below.

[Chemical Formula 16]

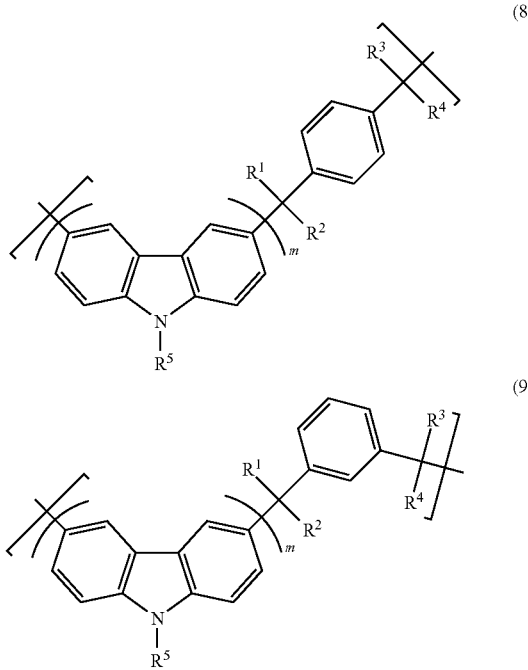

In the formulas, $R^1$ to $R^5$ and m are the same as above.

The weight-average molecular weight of the carbazole polymer of the invention, although not particularly limited, is preferably between 500 and 500,000, more preferably between 2,000 and 300,000, and even more preferably between 5,000 and 200,000.

In this invention, "weight-average molecular weight" refers to the weight-average molecular weight measured by gel permeation chromatography (GPC) against a polystyrene standard.

The carbazole polymer of the invention may be prepared by polymerizing a carbazole derivative of formula (10) below with a bisalcohol compound of formula (11) below in the presence of an acid catalyst.

[Chemical Formula 17]

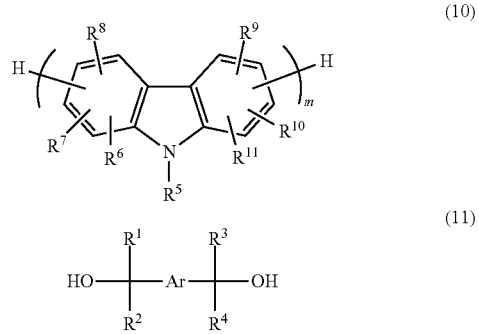

In the formulas, $R^1$ to $R^{11}$ and m are as defined above.

The charging amounts of the carbazole derivative of formula (10) and the bisalcohol compound of formula (11) may be set so that the amount of bisalcohol compound is from about 0.1 mole to about 10 mole, and preferably from about 1 mole to about 5 mole, per mole of the carbazole derivative.

The acid catalyst used in the polymerization reaction may be, for example, an inorganic acid such as hydrochloric acid or sulfuric acid, a solid acid such as a heteropoly acid or a cation exchange resin, or an organic acid such as a fatty acid or a sulfonic acid.

Examples of fatty acids include formic acid, acetic acid and propionic acid. Examples of sulfonic acids include benzenesulfonic acid, p-toluenesulfonic acid, methanesulfonic acid, ethanesulfonic acid and trifluoromethanesulfonic acid.

The acid catalyst is used in an amount of preferably from 0.1 to 200 mol %, and especially from 20 to 100 mol %, relative to the bisalcohol compound.

The polymerization reaction may be carried out in a solvent. When a solvent is used, so long as the type of solvent is one that has no adverse influence on the reaction, use may be made of any of various types of solvents commonly used in this sort of reaction.

Illustrative examples include alcohols (e.g., methanol, ethanol, propanol, butanol, octanol), cellosolves (e.g., methoxy ethanol, ethoxy ethanol), aprotic polar organic solvents (e.g., dimethylformamide, dimethylsulfoxide, dimethylacetamide, tetramethylurea, sulfolane, N-methylpyrrolidone, N,N-dimethylimidazolidinone), ethers (e.g., diethyl ether, diisopropyl ether, t-butyl methyl ether, tetrahydrofuran, dioxane), aliphatic hydrocarbons (e.g., pentane, hexane, c-hexane, octane, decane, decalin, petroleum ether), aromatic hydrocarbons (e.g., benzene, chlorobenzene, o-dichlorobenzene, nitrobenzene, toluene, xylene, mesitylene, tetralin), halogenated hydrocarbons (e.g., chloroform, dichloromethane, dichloroethane, carbon tetrachloride), ketones (e.g., acetone, methyl ethyl ketone, methyl butyl ketone, methyl isobutyl ketone), alkoxyalkanes (e.g., dimethoxyethane, diethoxyethane) and nitriles (e.g., acetonitrile, propionitrile, butyronitrile). These may be used singly or two or more may be used in admixture.

The reaction temperature may be suitably set in the range of from the melting point of the solvent used to the boiling point of the solvent, with a temperature of from about 30° C. to about 200° C. being preferred, and a temperature of from 50° C. to 150° C. being more preferred.

Following reaction completion, the target carbazole polymer can be obtained by work-up in the usual manner.

Because the above-described carbazole polymer of the invention, in addition to being a polymeric compound having electrochemically active sites in a non-conjugated form, has a stable oxidation state and exhibits a stable redox behavior, it can be advantageously used as an electrode active material (especially a positive electrode active material) for organic electrical storage devices such as lithium ion secondary batteries.

In such cases, an electrode in which an active material layer has been formed can be produced by mixing together an active material composed of the inventive carbazole polymer with, as needed, a second active material, a conductive additive, a binder resin and a solvent so as to prepare an electrode slurry, applying the slurry onto a current collector, and then drying the applied slurry in air or under heating.

Various types of active materials hitherto used in electrodes for electrical storage devices may be used as the second active material.

For example, in the case of lithium secondary batteries and lithium ion secondary batteries, chalcogen compounds capable of lithium ion insertion and extraction, lithium ion-containing chalcogen compounds, polyanion compounds, elemental sulfur and sulfur compounds may be used as the positive electrode active material.

Illustrative examples of such chalcogen compounds capable of lithium ion insertion and extraction include $FeS_2$, $TiS_2$, $MoS_2$, $V_2O_6$, $V_6O_{13}$ and $MnO_2$.

Illustrative examples of lithium ion-containing chalcogen compounds include $LiCoO_2$, $LiMnO_2$, $LiMn_2O_4$, $LiMo_2O_4$, $LiV_3O_8$, $LiNiO_2$ and $Li_xNi_yM_{1-y}O_2$ (wherein M is at least one metal element selected from among cobalt, manganese, titanium, chromium, vanadium, aluminum, tin, lead and zinc; and the conditions $0.05 \leq x \leq 1.10$ and $0.5 \leq y \leq 1.0$ are satisfied).

Illustrative examples of sulfur compounds include $Li_2S$ and rubeanic acid.

Exemplary negative electrode active materials include alkali metals, alkali alloys, at least one elemental substance selected from among group 4 to 15 elements of the periodic table which insert and extract lithium ions, as well as oxides, sulfides and nitrides thereof, and carbon materials which are capable of reversibly inserting and extracting lithium ions.

Illustrative examples of alkali metals include lithium, sodium and potassium. Illustrative examples of alkali metal alloys include metallic lithium, Li—Al, Li—Mg, Li—Al—Ni, sodium, Na—Hg and Na—Zn.

Illustrative examples of at least one elemental substance selected from among group 4 to 15 elements of the periodic table which insert and extract lithium ions include silicon, tin, aluminum, zinc and arsenic.

Illustrative examples of oxides include tin silicon oxide ($SnSiO_3$), lithium bismuth oxide ($Li_3BiO_4$), lithium zinc oxide ($Li_2ZnO_2$) and lithium titanium oxide ($Li_4Ti_5O_{12}$).

Illustrative examples of sulfides include lithium iron sulfides ($Li_xFeS_2$ ($0 \leq x \leq 3$)) and lithium copper sulfides ($Li_xCuS$ ($0 \leq x \leq 3$)).

Exemplary nitrides include lithium-containing transition metal nitrides, illustrative examples of which include $Li_xM_yN$ (wherein M is cobalt, nickel or copper; $0 \leq x \leq 3$, and $0 \leq y \leq 0.5$) and lithium iron nitride ($Li_3FeN_4$).

Examples of carbon materials which are capable of reversibly inserting and extracting lithium ions include graphite, carbon black, coke, glassy carbon, carbon fibers, carbon nanotubes, and sintered compacts of these.

In the case of electrical double-layer capacitors, a carbonaceous material may be used as the second active material.

The carbonaceous material is exemplified by activated carbon, such as activated carbon obtained by carbonizing a phenolic resin, then subjecting the carbonized resin to activation treatment.

Illustrative examples of conductive additives include carbon black, ketjen black, acetylene black, carbon whiskers, carbon fibers, carbon nanotubes, natural graphite, synthetic graphite, titanium oxide, ruthenium oxide, aluminum and nickel.

A known material may be suitably selected and used as the binder resin. Illustrative examples of such binder resins include electrically conductive polymers such as polyvinylidene fluoride (PVdF), polytetrafluoroethylene, tetrafluoroethylene-hexafluoropropylene copolymer, vinylidene fluoride-hexafluoropropylene copolymer (P(VDF-HFP)), vinylidene fluoride-chlorotrifluoroethylene copolymer (P(VDF-CTFE)), polyvinyl alcohol, polyimide, ethylene-propylene-diene ternary copolymers, styrene-butadiene rubbers, carboxymethyl cellulose (CMC), polyacrylic acid (PAA) and polyaniline.

The amount of binder resin added per 100 parts by weight of the active material is from 0.1 to 200 parts by weight, and especially from 1 to 100 parts by weight.

Illustrative examples of the solvent include water and the following organic solvents: ethers such as tetrahydrofuran (THF), diethyl ether and 1,2-dimethoxyethane (DME); halogenated hydrocarbons such as methylene chloride, chloroform and 1,2-dichloroethane; amides such as N,N-dimethylformamide (DMF), N,N-dimethylacetamide (DMAc) and N-methyl-2-pyrrolidone (NMP); ketones such as acetone, methyl ethyl ketone, methyl isobutyl ketone and cyclohexanone; alcohols such as methanol, ethanol, isopropanol and n-propanol; aliphatic hydrocarbons such as n-heptane, n-hexane and cyclohexane; aromatic hydrocarbons such as benzene, toluene, xylene and ethyl benzene; glycol ethers such as ethylene glycol monoethyl ether, ethylene glycol monobutyl ether and propylene glycol monomethyl ether; and glycols such as ethylene glycol and propylene glycol. The solvent may be suitably selected from among these according to the type of binder, although NMP is preferred in the case of water-insoluble binders such as PVdF, and water is preferred in the case of water-soluble binders such as PAA.

A material that has hitherto been used as the current collector in electrodes for electrical storage devices may be suitably selected and used as the current collector. Illustrative examples include thin films of copper, aluminum, nickel, gold, silver and alloys of these, carbon materials, metal oxides and electrically conductive polymers. In addition, an electrically conductive binder layer may be formed on the current collector.

The thickness thereof, although not subject to any particular limitation, is generally from about 1 μm to about 100 μm.

Illustrative examples of the method of applying the electrode slurry include spin coating, dip coating, flow coating, ink jet printing, spray coating, bar coating, gravure coating, slit coating, roll coating, flexographic printing, transfer printing, brush coating, blade coating and air knife coating. From the standpoint of work efficiency and other considerations, slit coating, bar coating, blade coating, roll coating, gravure coating and flexographic printing are preferred.

The temperature when drying under applied heat is generally from about 50° C. to about 200° C., and preferably from about 80° C. to about 150° C.

The organic electrical storage device according to the invention includes the above-described electrode. More specifically, it is constructed of at least a pair of positive and negative electrodes, a separator interposed between these electrodes, and an electrolyte, with at least one of the positive and negative electrodes being composed of the above-described electrode for organic electrical storage devices.

Because this organic electrical storage device is characterized by using as the active material a carbazole polymer having electrochemically active sites in a non-conjugated form, the separator, electrolyte and other constituent members of the device may be selected for use here from among known materials.

Illustrative examples of the separator include cellulose-based separators and polyolefin-based separators.

The electrolyte may be either a liquid or a solid, and moreover may be either aqueous or non-aqueous, the inventive electrode for organic electrical storage devices being able to exhibit a performance that is adequate for practical purposes even when employed in devices that use a non-aqueous electrolyte.

The non-aqueous electrolyte is exemplified by a non-aqueous electrolyte solution obtained by dissolving an electrolyte salt in a non-aqueous organic solvent.

Illustrative examples of electrolyte salts include lithium salts such as lithium tetrafluoroborate, lithium hexafluorophosphate, lithium perchlorate and lithium trifluoromethanesulfonate; and quaternary ammonium salts such as tetramethylammonium hexafluorophosphate, tetraethylammononium hexafluorophosphate, tetrapropylammonium hexafluorophosphate, methyltriethylammonium hexafluorophosphate, tetraethylammonium tetrafluoroborate and tetraethylammonium perchlorate.

Illustrative examples of non-aqueous organic solvents include alkylene carbonates such as propylene carbonate, ethylene carbonate and butylene carbonate; dialkyl carbonates such as dimethyl carbonate, methyl ethyl carbonate and diethyl carbonate; nitriles such as acetonitrile, and amides such as dimethylformamide.

EXAMPLES

The invention is illustrated more fully below by way of Working Examples and Comparative Examples, although the invention is not limited by these Examples. The instruments used for measurement in the Examples were as follows.

[1] $^1$H-NMR
  Instruments: AVANCE 500 (Bruker Corporation)
    JNM-LA400 (JEOL Datum)
  Solvents used in measurement:
    $CDCl_3$, DMSO-$d_6$
  Reference material: Tetramethylsilane (TMS) ($\delta$=0.0 ppm)

[2] Gel Permeation Chromatography (GPC)
  Instrument: HLC8220 GPC (Tosoh Corporation)
  Columns: Shodex KF-804L+KF-805L (Showa Denko K.K.)
  Column temperature: 40° C.
  Solvent: Tetrahydrofuran
  Detector: UV (254 nm)
  Calibration curve: polystyrene standard

[3] Electrochemical Measurements
  Instrument: ALS Model 660E (BAS Inc.)
  Solvent: Dichloromethane
  Electrolyte: Tetrabutylammonium hexafluorophosphate,
  Working electrode: Glassy carbon electrode
  Counterelectrode: Platinum electrode
  Reference electrode: silver/silver nitrate (acetonitrile solution containing 0.01 M of silver nitrate and 0.1 M of tetrabutylammonium perchlorate) electrode
  Scan rate: 200 mV/s

[4] Micrometer (for measuring thickness of active layer)
  Instrument: IR54 (Mitutoyo Corporation)

[5] Roll Press (for pressure bonding the electrodes)
  Apparatus: HSR-60150H (Hosen KK)

[6] Charge-Discharge Measurement System (for testing secondary batteries)
  Instrument: TOSCAT-3100 (Toyo System Co., Ltd.)

Synthesis Example 1

Synthesis of $(Cz)_2$

[Chemical Formula 18]

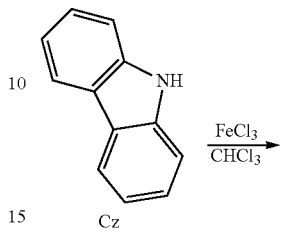

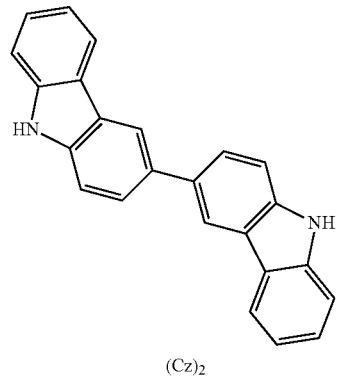

Carbazole (Cz, from Tokyo Chemical Industry Co., Ltd.) (8.36 g, 50 mmol) and iron chloride ($FeCl_3$, from Wako Pure Chemical Industries, Ltd.) (24.3 g, 150 mmol) were added to chloroform (Junsei Chemical Co., Ltd.; 150 mL), and the mixture was stirred 2.5 hours at room temperature. The reaction solvent was distilled off with a rotary evaporator, following which methanol (Junsei Chemical Co., Ltd.; 200 mL) was added, the mixture was stirred 4 hours at 70° C., and the insoluble matter was separated off and collected. To this was once again added methanol (200 mL), followed by 4 hours of stirring at 70° C., after which the insoluble matter was separated off and collected, giving the target compound (Cz)$_2$ (7.73 g, 92%). The results obtained by measurement of the $^1$H-NMR spectrum (DMSO-$d_6$) are shown in FIG. 1.

Synthesis Example 2

Synthesis of $(TEGCz)_2$

[Chemical Formula 19]

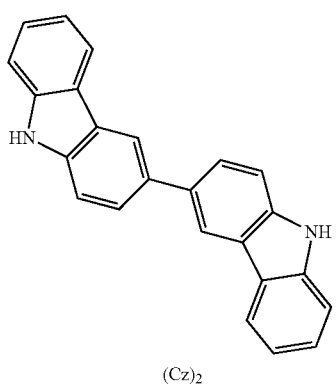

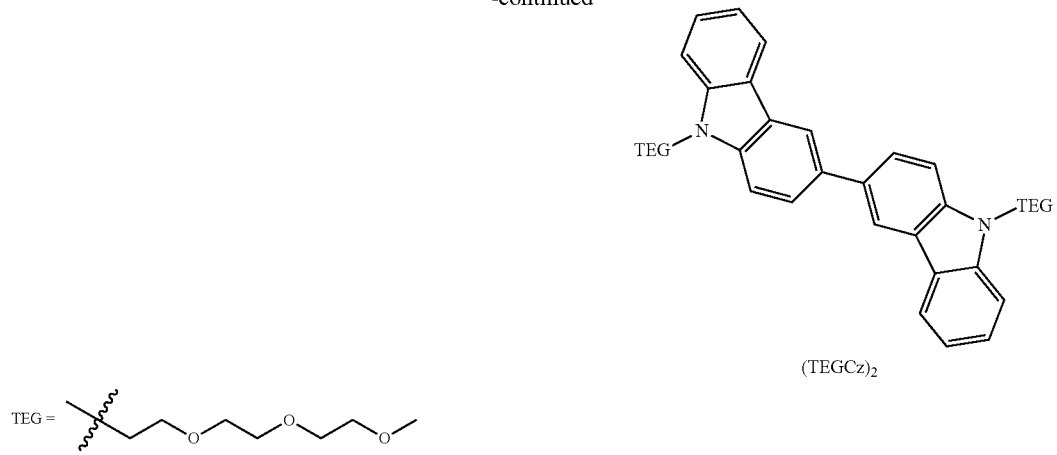

(TEGCz)₂

TEG = 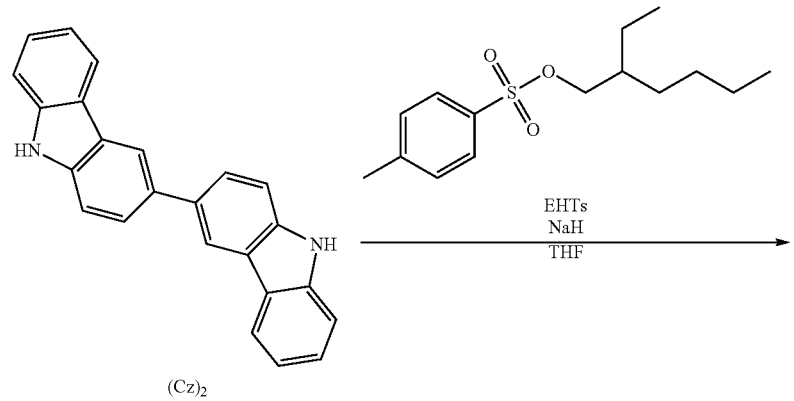

Figure 2:
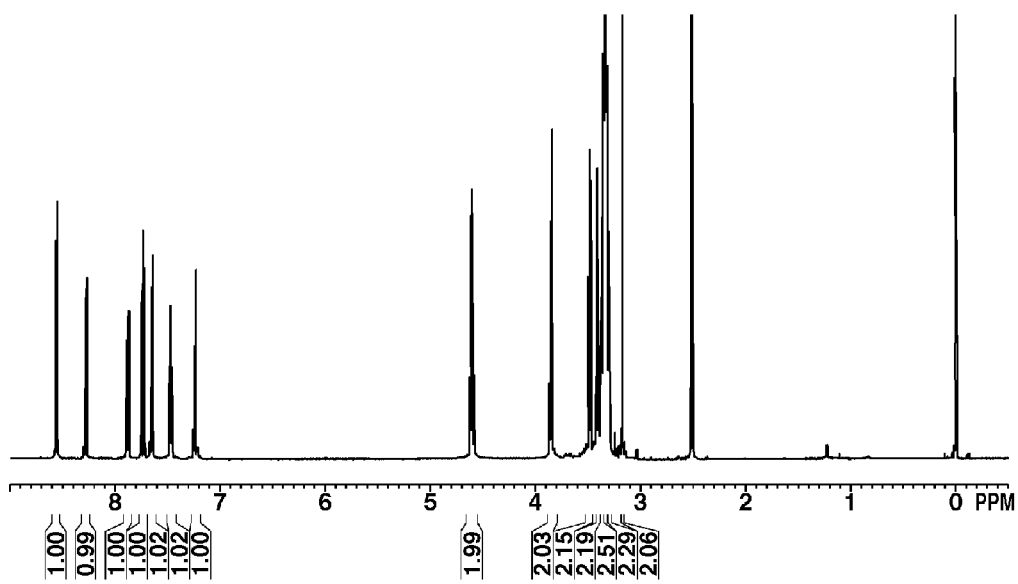
FIG. 2 is an $^1$H-NMR spectrum of the (TEGCz)$_2$ prepared in Synthesis Example 2.

The (Cz)₂ obtained in Synthesis Example 1 (1.00 g, 3.00 mmol), sodium hydride (Wako Pure Chemical Industries, Ltd.; 50% in oil; 0.35 g, 7.29 mmol) and TEGTs (2.39 g, 7.50 mmol) were added to DMF (Junsei Chemical Co., Ltd.; 10 mL), and the mixture was stirred 2 hours at 90° C. The solvent was driven off under reduced pressure, following which purification was carried out by column chromatography (SiO₂, chloroform/ethyl acetate=90/10 (v/v)), giving the target compound (0.91 g, 49%). The resulting compound was a liquid at normal temperature. The results obtained by measurement of the ¹H-NMR spectrum (DMSO-d₆) are shown in FIG. 2.

The TEGTs was synthesized while referring to the method described in *Dalton Trans.*, 9043 (2009).

Synthesis Example 3

Synthesis of (EHCz)₂

[Chemical Formula 20]

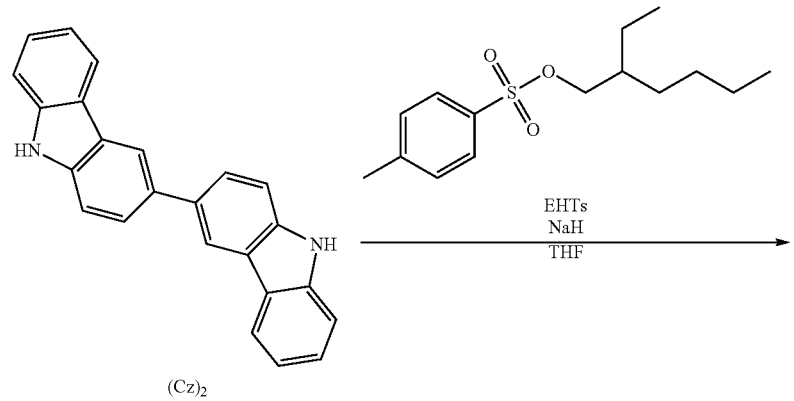

(Cz)₂

→ EHTs / NaH / THF

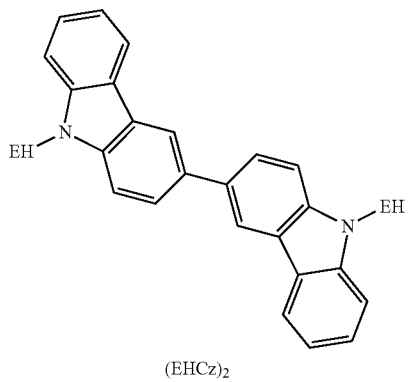

(EHCz)₂

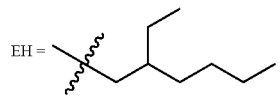

Figure 3:
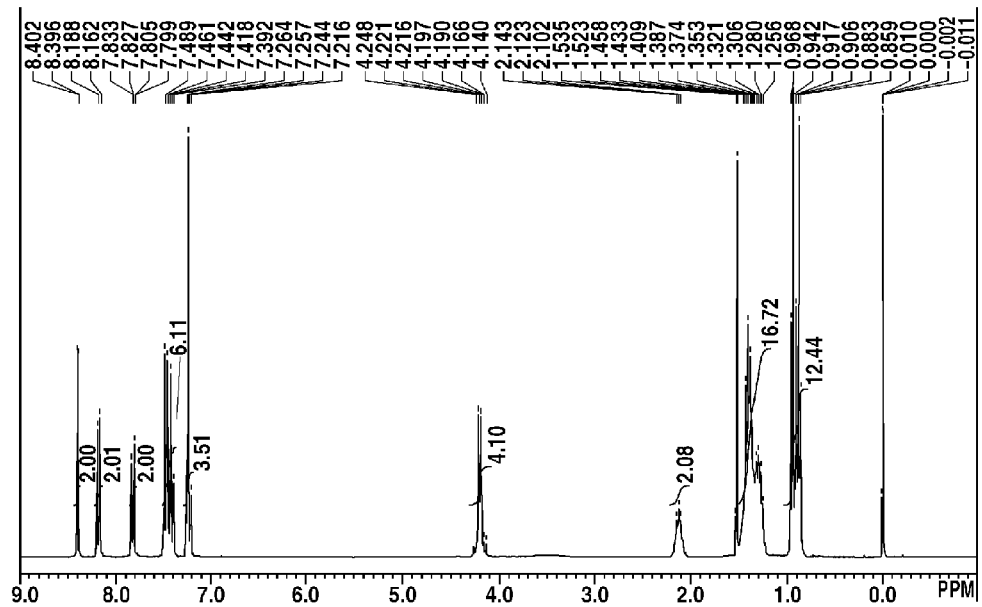
FIG. 3 is an ¹H-NMR spectrum of the (EHCz)₂ prepared in Synthesis Example 3.

The (Cz)$_2$ obtained in Synthesis Example 1 (10.0 g, 30.1 mmol), sodium hydride (Wako Pure Chemical Industries, Ltd.; 60% in oil; 2.65 g, 66.2 mmol) and EHTs (18.8 g, 66.2 mmol) were added to THF (Junsei Chemical Co., Ltd.; 300 mL), and the mixture was stirred 19 hours under refluxing. The mixture was then cooled to room temperature, ethyl acetate (Junsei Chemical Co., Ltd.; 200 mL) and water (200 mL) were added, and liquid separation was effected. The aqueous phase was extracted with ethyl acetate (200 mL, twice), following which the combined organic phases were washed with saturated saline (500 mL). The washed organic phase was dehydrated with magnesium sulfate (Junsei Chemical Co., Ltd.), following which the solvent was driven off by distillation. Purification was carried out by column chromatography (SiO$_2$, hexane/ethyl acetate=100/0 to 98/2 (v/v)), followed by recrystallization from hexane, giving the target compound as a white solid (8.68 g, 52%). The results obtained by measurement of the $^1$H-NMR spectrum (CDCl$_3$) are shown in FIG. 3.

The EHTs was synthesized while referring to the method described in *Dalton Trans.*, 3955 (2009).

Example 1

Synthesis of P(TEGCz-mDMMB)

[Chemical Formula 21]

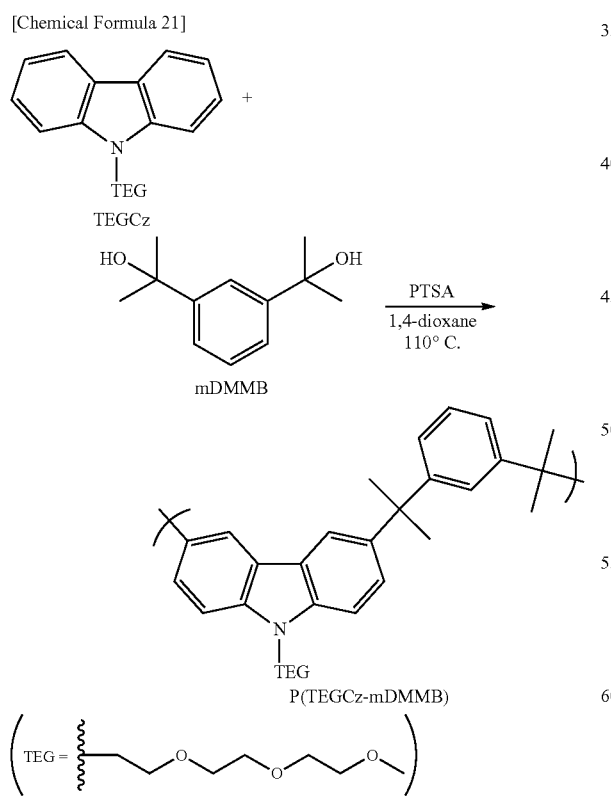

Figure 4:
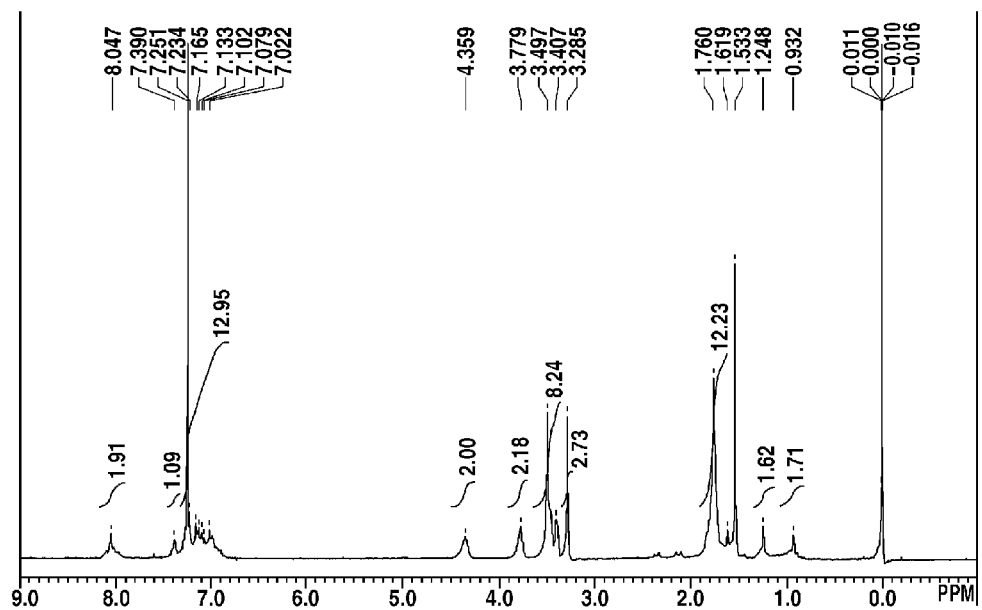
FIG. 4 is an ¹H-NMR spectrum of the P(TEGCz-mDMMB) prepared in Example 1.

TEGCz synthesized by the method described in *Synthetic Metals*, 89(3), 171 (1997) (500 mg, 1.60 mmol), α,α'-dihydroxy-1,3-diisopropylbenzene (abbreviated below as "mDMMB"; from Tokyo Chemical Industry Co., Ltd.) (527 mg, 2.71 mmol) and p-toluenesulfonic acid monohydrate (abbreviated below as "PTSA"; from Tokyo Chemical Industry Co., Ltd.) (303 mg, 1.60 mmol) were added to 1,4-dioxane (Junsei Chemical Co., Ltd.; 1 g), and the mixture was stirred 4.5 hours at 110° C. After cooling to room temperature, the mixture was diluted by adding THF (Junsei Chemical Co., Ltd.; 6 g). This dilution was added dropwise to a mixed solution of methanol (Junsei Chemical Co., Ltd.; 30 g), water (7 g) and 28% ammonia water (Junsei Chemical Co., Ltd.; 5 g), thereby carrying out re-precipitation. The precipitate was filtered, then vacuum-dried, giving 887 mg of P(TEGCz-mDMMB) as a white solid. The results obtained from measurement of the $^1$H-NMR spectrum (CDCl$_3$) are shown in FIG. 4. The polystyrene-equivalent weight-average molecular weight Mw of the resulting P(TEGCz-mDMMB), as measured by gel permeation chromatography, was 91,700, and the polydispersity Mw/Mn was 9.6.

Example 2

Synthesis of P(TEGCz-pDMMB)

[Chemical Formula 22]

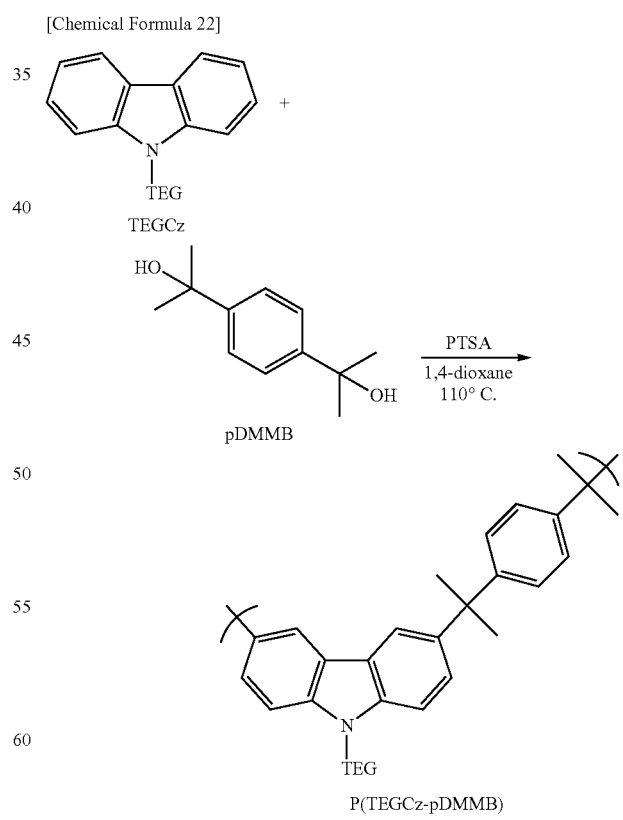

Figure 5:
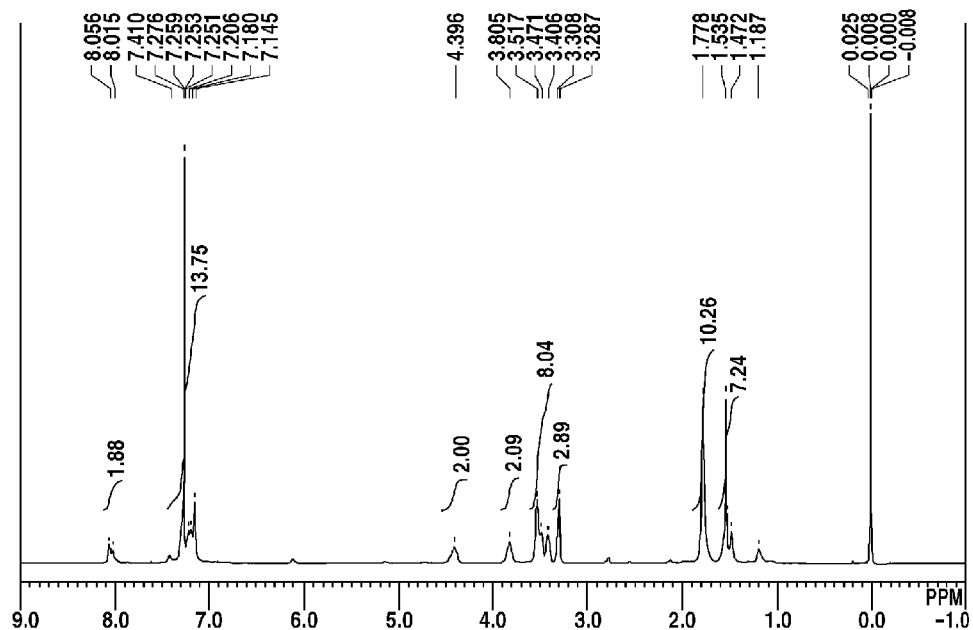
FIG. 5 is an ¹H-NMR spectrum of the P(TEGCz-pDMMB) prepared in Example 2.

TEGCz (500 mg, 1.60 mmol), α,α'-dihydroxy-1,4-diisopropylbenzene (abbreviated below as "pDMMB"; from Tokyo Chemical Industry Co., Ltd.) (527 mg, 2.71 mmol) and PTSA (303 mg, 1.60 mmol) were added to 1,4-dioxane (1 g), and the mixture was stirred 2 hours at 110° C. After cooling to room temperature, the mixture was diluted by adding THF (6 g). This dilution was added dropwise to a mixed solution of methanol (30 g), water (7 g) and 28% ammonia water (5 g), thereby carrying out re-precipitation. The precipitate was filtered, then vacuum-dried, giving 813 mg of P(TEGCz-pDMMB) as a white solid. The results obtained by measurement of the $^1$H-NMR spectrum (CDCl$_3$) are shown in FIG. 5. The polystyrene-equivalent weight-average molecular weight Mw, as measured by gel permeation chromatography, was 17,500, and the polydispersity Mw/Mn was 3.4.

Example 3

Synthesis of P(TEGCz2-mDMMB)

[Chemical Formula 23]

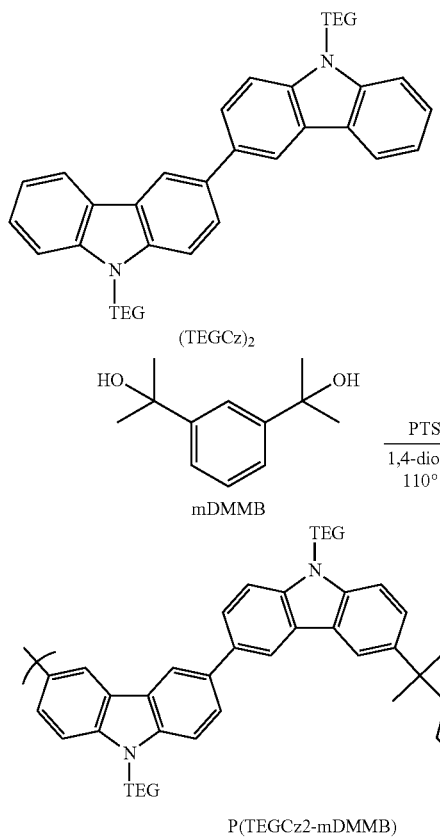

P(TEGCz2-mDMMB)

Figure 6:
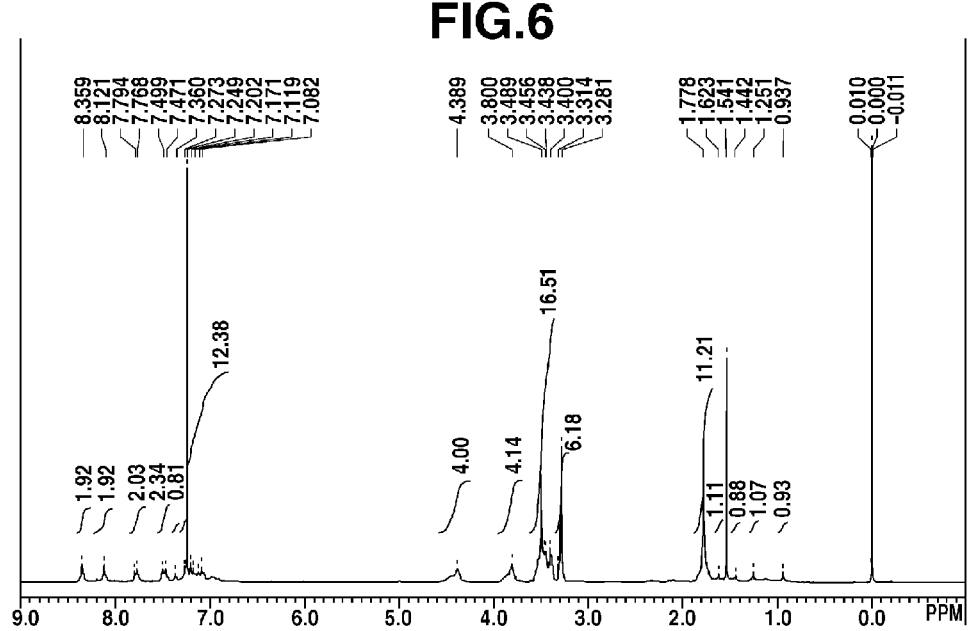
FIG. 6 is an ¹H-NMR spectrum of the P(TEGCz2-mDMMB) prepared in Example 3.

(TEGCz)$_2$ (500 mg, 0.800 mmol), mDMMB (264 mg, 1.36 mmol) and PTSA (152 mg, 0.800 mmol) were added to 1,4-dioxane (0.75 g), and the mixture was stirred 6 hours at 110° C. After cooling to room temperature, the mixture was diluted by adding THF (6 g). This dilution was added dropwise to a mixed solution of methanol (30 g), water (7 g) and 28% ammonia water (5 g), thereby carrying out re-precipitation. The precipitate was filtered, then vacuum-dried, giving 671 mg of P(TEGCz2-mDMMB) as a white solid. The results obtained from measurement of the $^1$H-NMR spectrum (CDCl$_3$) are shown in FIG. 6. The polystyrene-equivalent weight-average molecular weight Mw, as measured by GPC, was 51,900, and the polydispersity Mw/Mn was 6.2.

Example 4

Synthesis of P(TEGCz2-pDMMB)

[Chemical Formula 24]

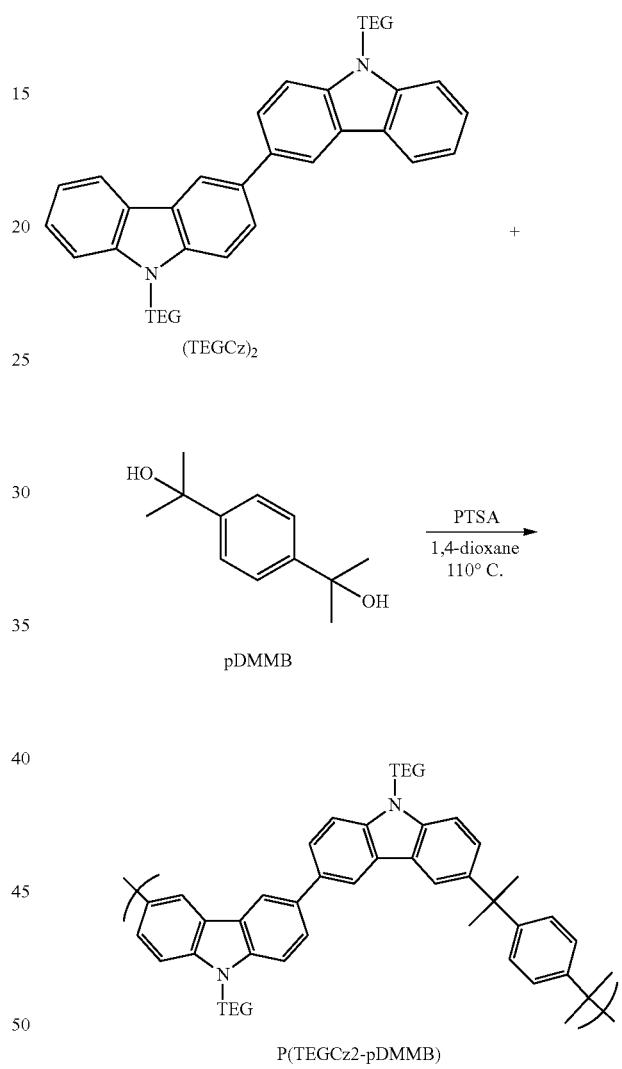

P(TEGCz2-pDMMB)

Figure 7:
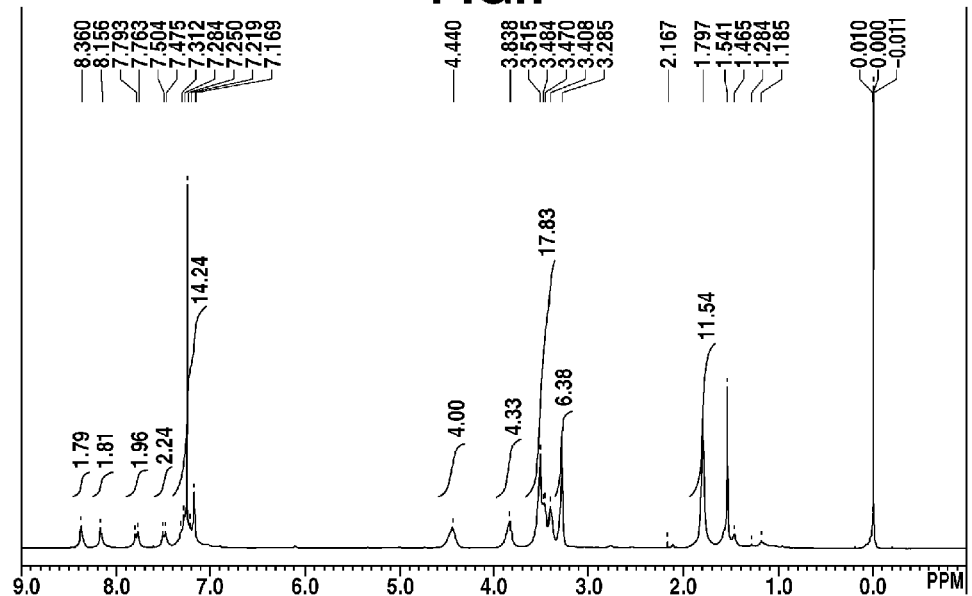
FIG. 7 is an ¹H-NMR spectrum of the P(TEGCz2-pDMMB) prepared in Example 4.

(TEGCz)$_2$ (500 mg, 0.800 mmol), pDMMB (264 mg, 1.36 mmol) and PTSA (152 mg, 0.800 mmol) were added to 1,4-dioxane (0.75 g), and the mixture was stirred 6 hours at 110° C. After cooling to room temperature, the mixture was diluted by adding THF (6 g). The insoluble matter was removed, following which the dilution was added dropwise to a mixed solution of methanol (30 g), water (7 g) and 28% ammonia water (5 g), thereby carrying out re-precipitation. The precipitate was filtered, then vacuum-dried, giving 433 mg of P(TEGCz2-pDMMB) as a white solid. The results obtained by measurement of the $^1$H-NMR spectrum (CDCl$_3$) are shown in FIG. 7. The polystyrene-equivalent weight-average molecular weight Mw, as measured by GPC, was 129,000, and the polydispersity Mw/Mn was 11.3.

Example 5

Synthesis of P(EHCz2-mDMMB)

[Chemical Formula 23]

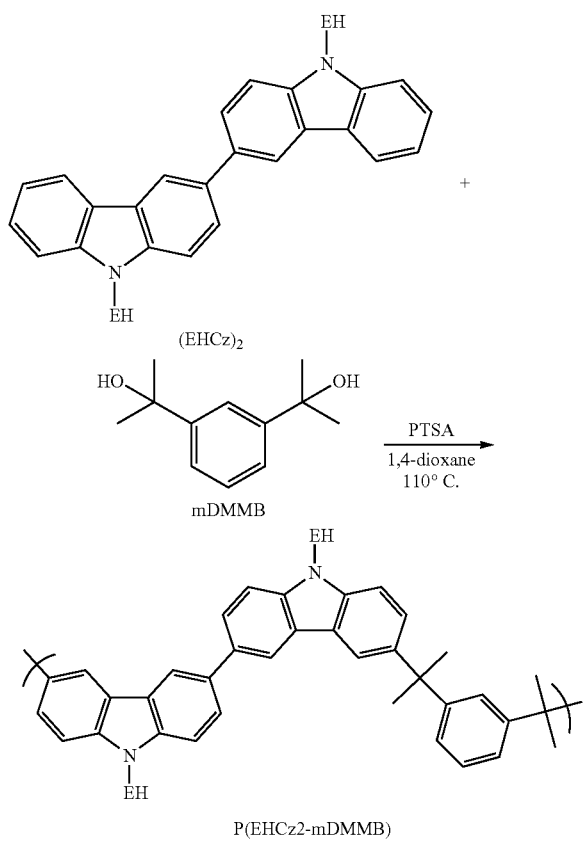

Figure 8:
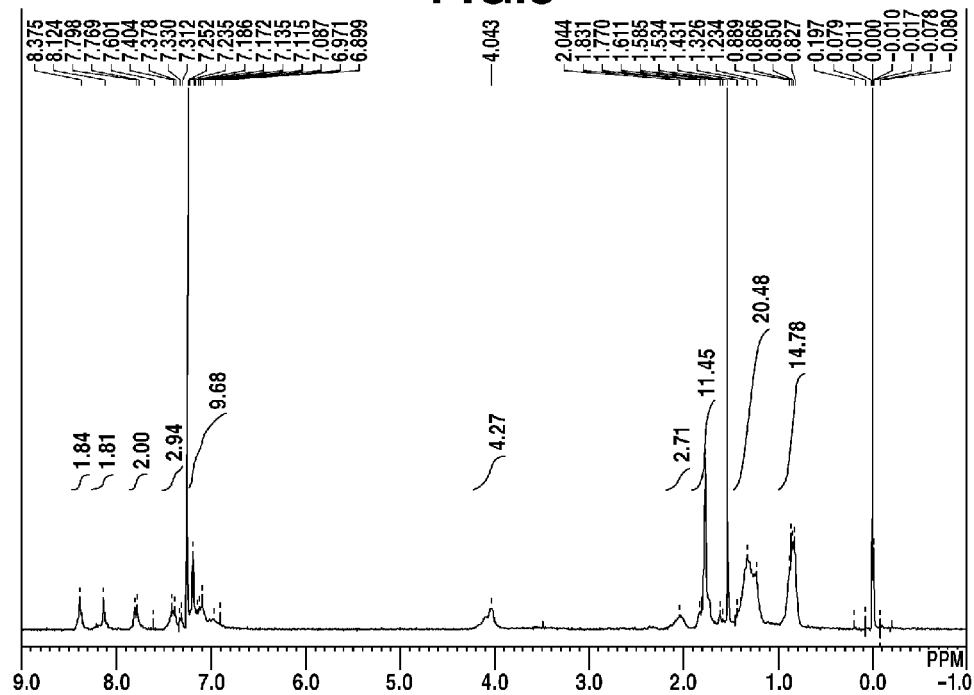
FIG. 8 is an ¹H-NMR spectrum of the P(EHCz2-mDMMB) prepared in Example 5.

(EHCz)₂ (500 mg, 0.898 mmol), mDMMB (297 mg, 1.53 mmol) and PTSA (171 mg, 0.898 mmol) were added to 1,4-dioxane (0.75 g), and the mixture was stirred 4 hours at 110° C. After cooling to room temperature, the mixture was diluted by adding THF (6 g). The dilution was added dropwise to a mixed solution of methanol (30 g), water (7 g) and 28% ammonia water (5 g), thereby carrying out re-precipitation. The precipitate was filtered, then vacuum-dried, giving 676 mg of P(EHCz2-mDMMB) as a white solid. The results obtained by measurement of the ¹H-NMR spectrum (CDCl₃) are shown in FIG. 8. The polystyrene-equivalent weight-average molecular weight Mw, as measured by GPC, was 45,200, and the polydispersity Mw/Mn was 5.9.

Comparative Example 1

Synthesis of P(TEGCz-PhCHO)

[Chemical Formula 26]

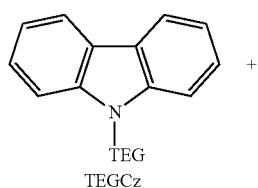

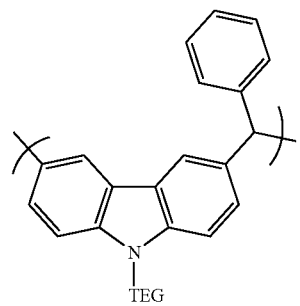

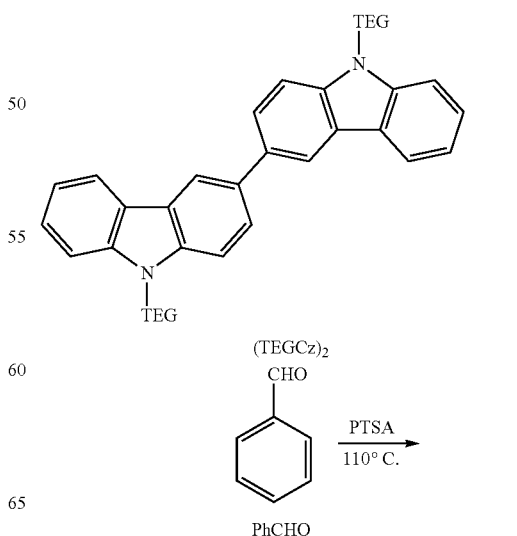

Figure 9:
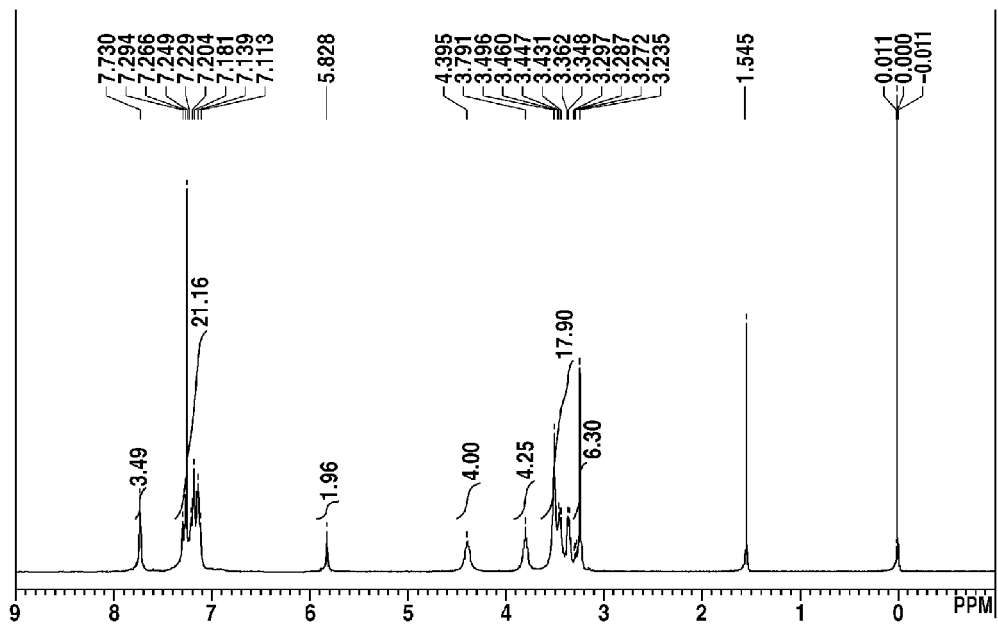
FIG. 9 is an ¹H-NMR spectrum of the P(TEGCz-PhCHO) prepared in Comparative Example 1.

TEGCz (500 mg, 1.60 mmol), benzaldehyde (abbreviated below as "PhCHO"; from Wako Pure Chemical Industries, Co., Ltd.) (500 mg, 4.71 mmol) and PTSA (121 mg, 0.638 mmol) were added to 1,4-dioxane (0.5 g), and the mixture was stirred 3 hours at 110° C. After cooling to room temperature, the mixture was diluted by adding THF (6 g). The dilution was added dropwise to a mixed solution of methanol (30 g), water (7 g) and 28% ammonia water (5 g), thereby carrying out re-precipitation. The precipitate was filtered, then vacuum-dried, giving 592 mg of P(TEGCz-PhCHO) as a white solid. The results obtained from measurement of the ¹H-NMR spectrum (CDCl₃) are shown in FIG. 9. The polystyrene-equivalent weight-average molecular weight Mw, as measured by GPC, was 70,000, and the polydispersity Mw/Mn was 8.8.

Comparative Example 2

Synthesis of P(TEGCz2-PhCHO)

[Chemical Formula 27]

-continued

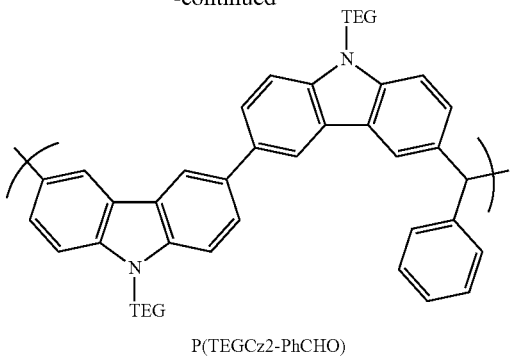

P(TEGCz2-PhCHO)

Figure 10:
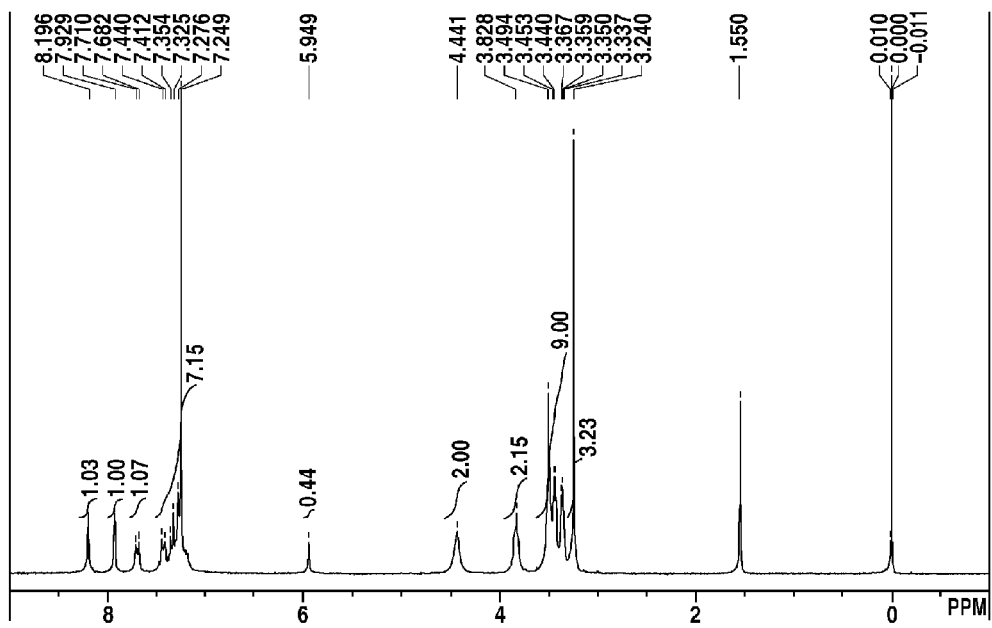
FIG. 10 is an ¹H-NMR spectrum of the P(TEGCz2-PhCHO) prepared in Comparative Example 2.

(TEGCz)$_2$ (500 mg, 0.800 mmol), PhCHO (1,250 mg, 11.8 mmol) and PTSA (30.4 mg, 0.160 mmol) were mixed together, and the mixture was stirred 3 hours at 110° C. After cooling to room temperature, the mixture was diluted by adding THF (6 g). The dilution was added dropwise to a mixed solution of methanol (30 g), water (7 g) and 28% ammonia water (5 g), thereby carrying out re-precipitation. The precipitate was filtered, then vacuum-dried, giving 490 mg of P(TEGCz2-PhCHO) as a white solid. The results obtained by measurement of the $^1$H-NMR spectrum (CDCl$_3$) are shown in FIG. 10. The polystyrene-equivalent weight-average molecular weight Mw, as measured by GPC, was 170,000, and the polydispersity Mw/Mn was 11.4.

Electrochemical measurement was carried out on the carbazole polymers synthesized in above Examples 1 to 5 and Comparative Examples 1 and 2. Cyclic voltammograms for each are shown in FIGS. 11 to 17, and the results are presented in Table 1.

Figure 18:
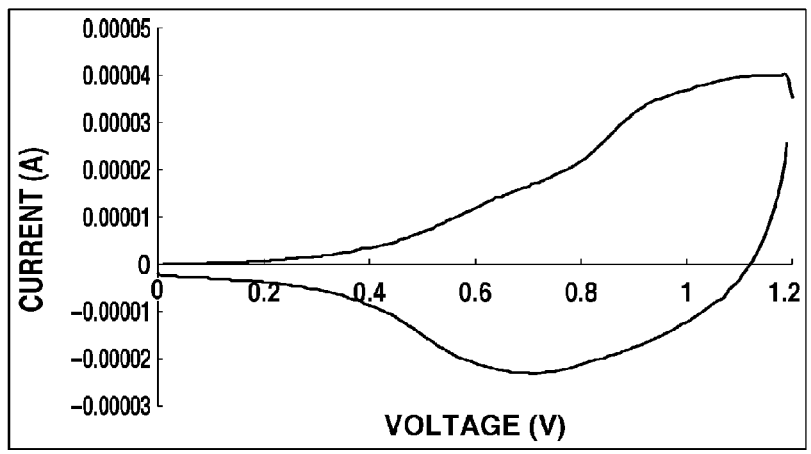
FIG. 18 is a cyclic voltammogram of polyvinyl carbazole.
Figure 19:
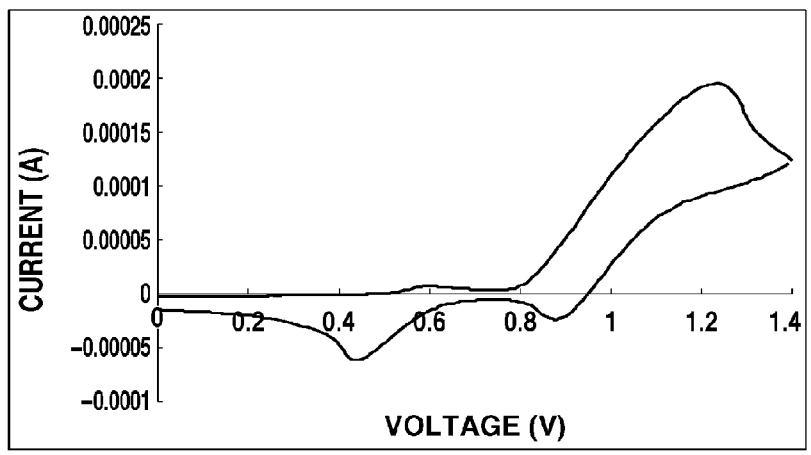
FIG. 19 is a cyclic voltammogram of TEGCz.
Figure 20:
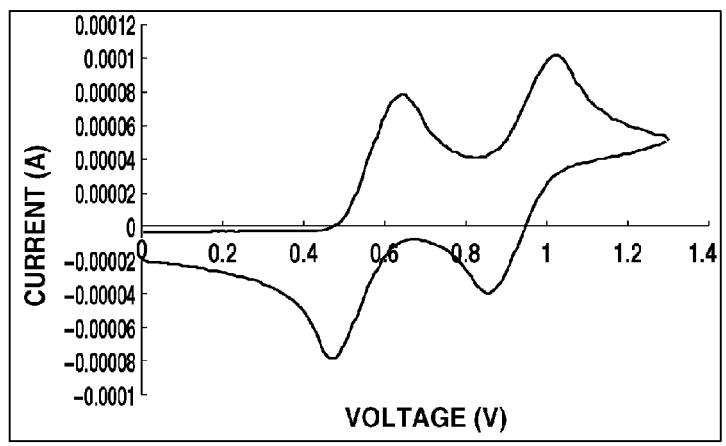
FIG. 20 is a cyclic voltammogram of the (TEGCz)₂ prepared in Synthesis Example 2.
Figure 21:
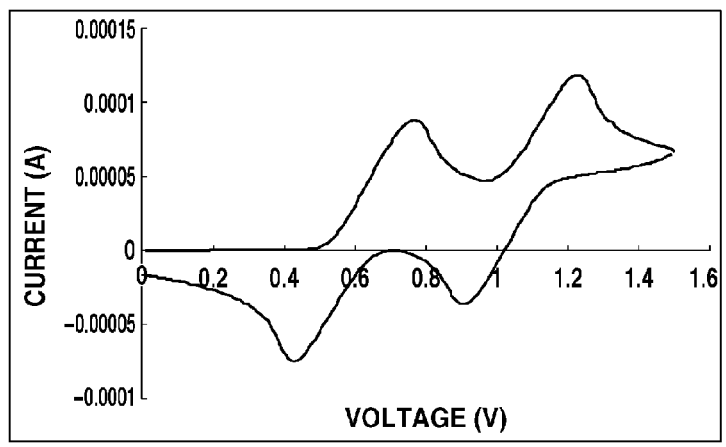
FIG. 21 is a cyclic voltammogram of the (EHCz)₂ prepared in Synthesis Example 3.

Also, for the sake of comparison, FIG. 18 shows the cyclic voltammogram for polyvinyl carbazole (Comparative Example 3), a general-purpose carbazole polymer. In addition, FIGS. 19 to 21 show cyclic voltammograms for TEGCz, (TEGCz)$_2$ and (EHCz)$_2$, which are the monomers from which the respective polymers were obtained.

of the oxidation wave and the reduction wave corresponding thereto are complex, from which it is apparent that a stable oxidation state does not form.

Figure 11:
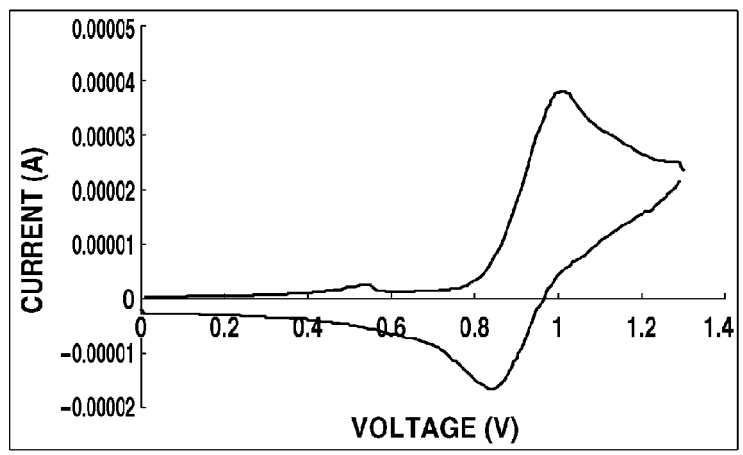
FIG. 11 is a cyclic voltammogram of the P(TEGCz-mDMMB) prepared in Example 1.
Figure 12:
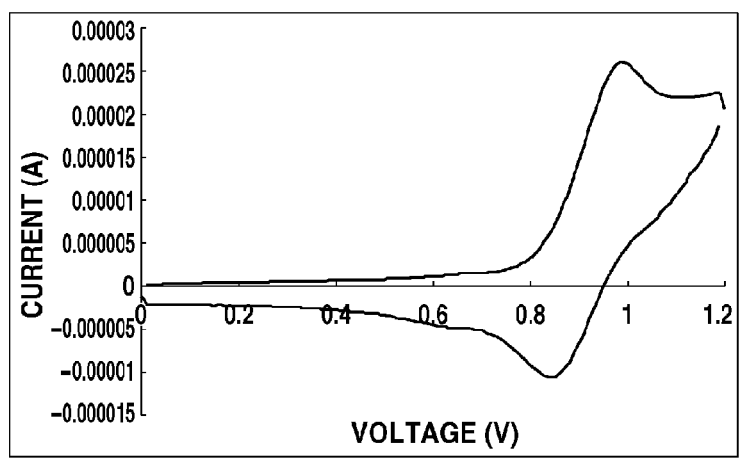
FIG. 12 is a cyclic voltammogram of the P(TEGCz-pDMMB) prepared in Example 2.
Figure 13:
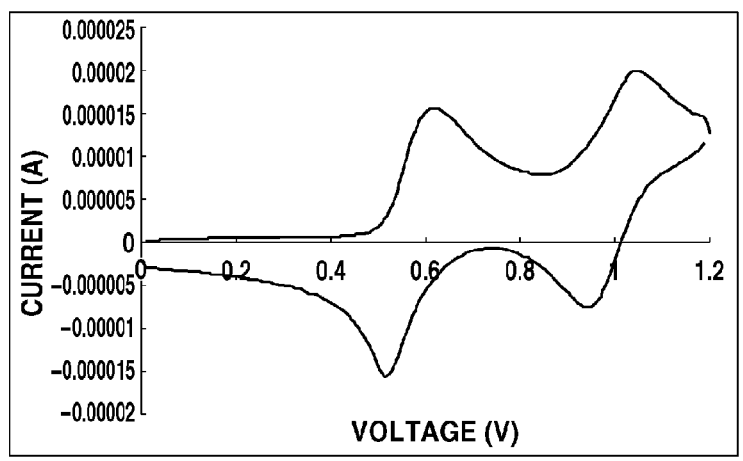
FIG. 13 is a cyclic voltammogram of the P(TEGCz2-mDMMB) prepared in Example 3.
Figure 14:
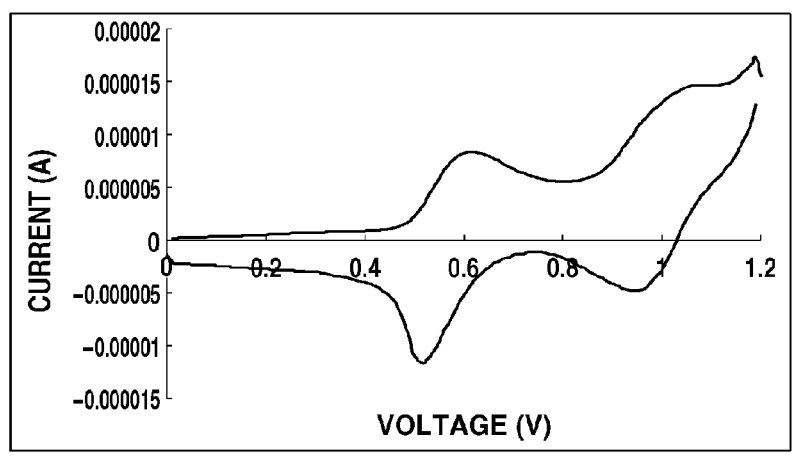
FIG. 14 is a cyclic voltammogram of the P(TEGCz2-pDMMB) prepared in Example 4.
Figure 15:
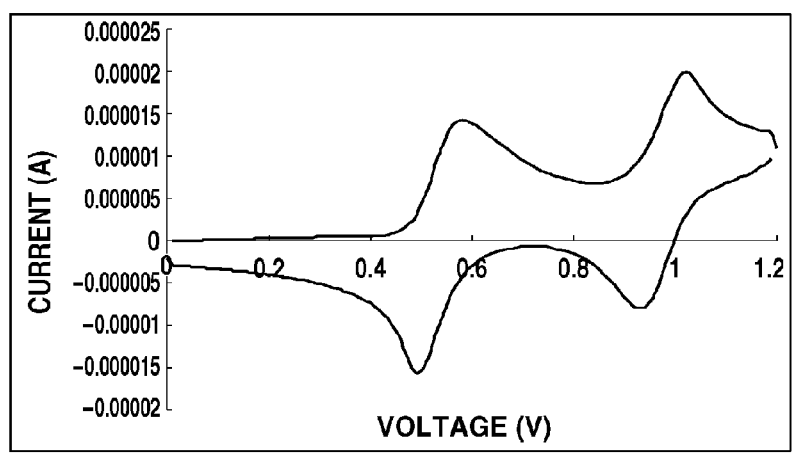
FIG. 15 is a cyclic voltammogram of the P(EHCz2-mDMMB) prepared in Example 5.

By contrast, as shown in FIGS. 11 and 12, reduction waves corresponding to oxidation are clearly observable for P(TEGCz-mDMMB) and P(TEGCz-pDMMB), from which it is apparent that the stability of the oxidation state has increased. In addition, as shown in FIGS. 13 to 15, reduction waves corresponding to oxidation are clearly observable for the polymers P(TEGCz2-mDMMB), P(TEGCz2-pDMMB) and P(EHCz2-mDMMB) obtained using (TEGCz)$_2$ and (EHCz)$_2$, which have stable oxidation states. Also, as shown in Table 1, in contrast with Examples 1 and 2, wherein the reduction current decreases to about one-third of the oxidation current, in Examples 3 to 5, because the current value for the oxidation wave and the current value for the reduction wave are substantially the same, it is apparent that the stability of the oxidation state has increased even more.

It was thus clearly shown that, by having the carbons bonded to carbazole be quaternary carbons, the oxidation state of the carbazole polymer stabilizes.

Example 6

Fabrication of Lithium Ion Battery Using P(TEGCz2-mDMMB)

The following ingredients were mixed together in a mortar so as to prepare an electrode slurry (solids concentration, 18 wt %; P(TEGCz2-mDMMB):PVdF:VGCF-H=20:20:60 (weight ratio)): the P(TEGCz2-mDMMB) synthesized in Example 3 (0.360 g), as the active material; an N-methyl-2-pyrrolidone (NMP) solution of polyvinylidene fluoride (PVdF) (12 wt %; KF Polymer L#1120, from Kureha Corporation) (3.00 g), as the binder; carbon nanotubes (VGCF-H, from Showa Denko K.K.) (1.08 g), as the conductive additive; and NMP (5.56 g).

The electrode slurry thus prepared was uniformly spread by the doctor blade method on aluminum foil (UACJ Foil

TABLE 1

| | Oxidation potential (V) | Oxidation current (×10$^{-5}$ A) | Reduction current (×10$^{-5}$ A) | Stability of oxidation state |
|---|---|---|---|---|
| Example 1 | 0.93 | 3.03 | −1.25 | good |
| Example 2 | 0.92 | 2.04 | −0.714 | good |
| Example 3 | 0.57 | 1.47 | −1.49 | very good |
| | 0.99 | 1.17 | −1.03 | |
| Example 4 | 0.57 | 0.687 | −0.873 | very good |
| | 1.01 | 0.805 | −0.688 | |
| Example 5 | 0.54 | 1.35 | 1.50 | very good |
| | 0.98 | 1.27 | −1.06 | |
| Comparative Example 1 | 1.01 (peak of oxidation wave) | 4.69 | none | poor |
| Comparative Example 2 | complex | complex | complex | fair |

Figure 16:
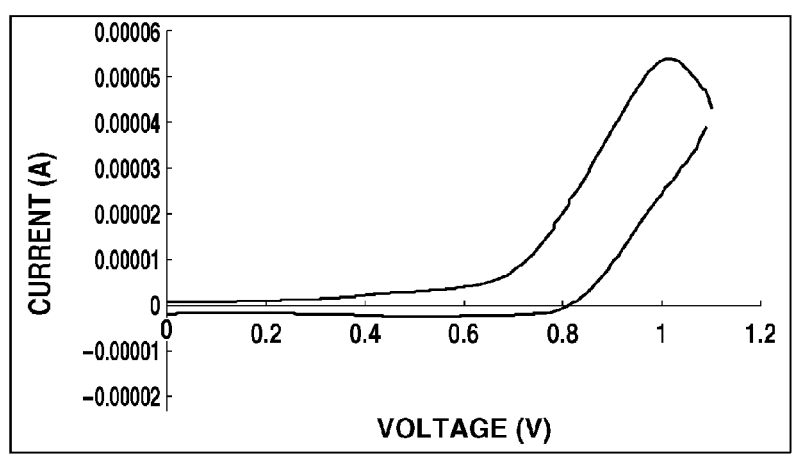
FIG. 16 is a cyclic voltammogram of the P(TEGCz-PhCHO) prepared in Comparative Example 1.
Figure 17:
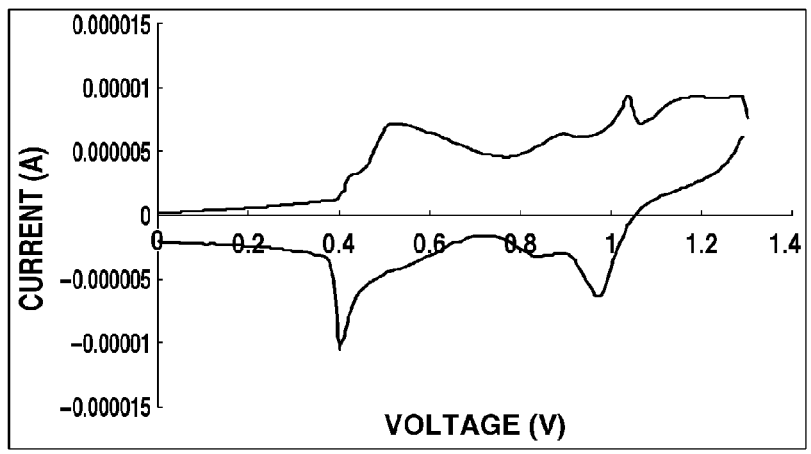
FIG. 17 is a cyclic voltammogram of the P(TEGCz2-PhCHO) prepared in Comparative Example 2.

As shown in FIG. 18, in the case of polyvinyl carbazole, which is a general-purpose carbazole, a reduction wave corresponding to oxidation is not clearly observable, from which it is apparent that the oxidation state is unstable. Also, as shown in FIG. 16, a reduction wave corresponding to oxidation is not observable whatsoever for P(TEGCz-PhCHO) as well. In addition, as shown in FIG. 17, even in the case of P(TEGCz2-PhCHO) obtained using as the monomer (TEGCz)$_2$, which has a stable oxidation state, the waveforms Corporation; thickness, 20 μm), after which it was dried at 80° C. for 30 minutes then at 120° C. for 30 minutes, and subsequently pressure-bonded with a roll press, thereby producing an electrode (wet (pre-drying) film thickness, 300 μm; film thickness after drying and pressure bonding, 40 μm).

The electrode thus produced was die-cut in the shape of a 10 mm diameter disk and the weight was measured, following which the electrode disk was vacuum-dried at 100° C. for 9 hours and transferred to a glovebox filled with argon.

A stack of six lithium foils that had been die-cut to a diameter of 14 mm (Honjo Chemical Corporation; thickness, 0.17 mm) was set in a 2032 coin cell (Hosen KK) case within a glovebox filled with argon, one piece of separator (Celgard 2400) die-cut to a diameter of 16 mm that had been permeated for at least 24 hours with an electrolyte solution (ethylene carbonate:diethyl carbonate=1:1 (volume ratio) solution containing 1 mol/L of the electrolyte lithium hexafluorophosphate, from Kishida Chemical Co., Ltd.) was placed on the foil, and the above electrode that had been die-cut in the shape of a disk was placed on top thereof with the electrode slurry-coated surface facing down.

Next, one drop of the electrolyte solution was added dropwise in the coin cell case, after which a gasket and a cover to which a washer and a spacer had been welded was placed on top, following which the cell was sealed with a coil cell crimper. This was then placed at rest for 24 hours, thereby giving a secondary battery for testing.

Comparative Example 3

Fabrication of Lithium Ion Battery Using P(TEGCz2-PhCHO)

Aside from using the P(TEGCz2-PhCHO) synthesized in Comparative Example 2 as the active material, a secondary battery for testing was fabricated in the same way as in Example 6.

Comparative Example 4

Fabrication of Lithium Ion Battery Using $(Cz)_2$

Aside from using the $(Cz)_2$ synthesized in Synthesis Example 1 as the active material, a secondary battery for testing was fabricated in the same way as in Example 6.

Figure 24:
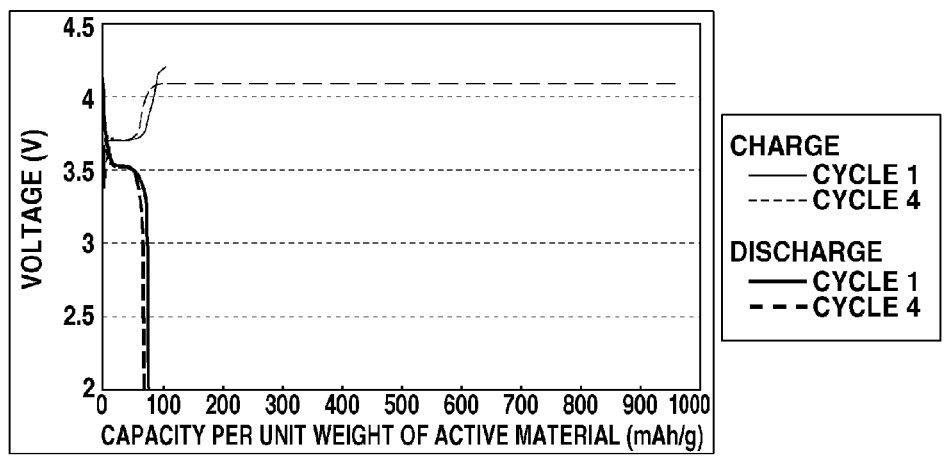
FIG. 24 is a graph showing charge/discharge curves for the first and fourth cycles of the lithium ion secondary battery fabricated in Comparative Example 4.
Figure 25:
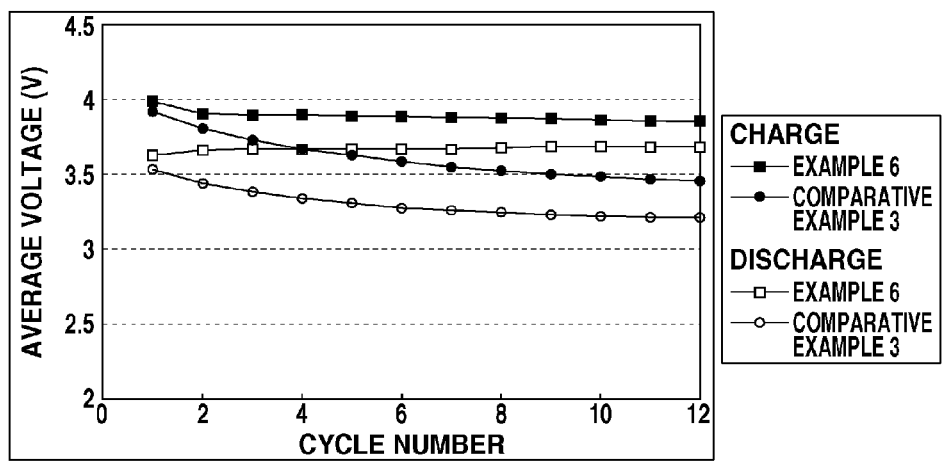
FIG. 25 is a graph showing the cycle characteristics in terms of average voltage for the lithium ion secondary batteries fabricated in Example 6 and Comparative Example 3.

The properties of the electrodes as positive electrodes for the lithium ion secondary batteries fabricated in Example 6 and Comparative Examples 3 and 4 were evaluated under the following test conditions.
  Current: 0.3° C. constant-current charge/discharge (the theoretical capacity of P(TEGCz2-mDMMB) was set to 68.5 mAh/g, the theoretical capacity of P(TEGCz2-PhCHO) was set to 75.2 mAh/g, and the theoretical capacity of $(Cz)_2$ was set to 161 mAh/g).
  Cut-off voltage: 4.2V to 2.0 V
  Temperature: room temperature Charge-discharge curves for the first, fourth and eighth cycles in Example 6 are shown in FIG. 22, charge-discharge curves for the first, fourth and eighth cycles in Comparative Example 3 are shown in FIG. 23, charge-discharge curves for the first and fourth cycles in Comparative Example 4 are shown in FIG. 24, and the average voltages for each cycle in the lithium ion secondary batteries fabricated in Example 6 and Comparative Example 3 are shown in FIG. 25.

In a lithium ion secondary battery in which a carbazole derivative that is not a polymer $((Cz)_2)$ was used, the voltage rose to 4.2 V in the first cycle. However, as is evident from the results for the fourth cycle, the voltage did not rise to 4.2 V in subsequent charging (FIG. 24). The reason is thought to be that, because the solubility of $(Cz)_2$ in the oxidation state is high, the $(Cz)_2$ dissolves into the electrolyte solution and reaches the negative electrode, thus giving rise to leakage.

Figure 23:
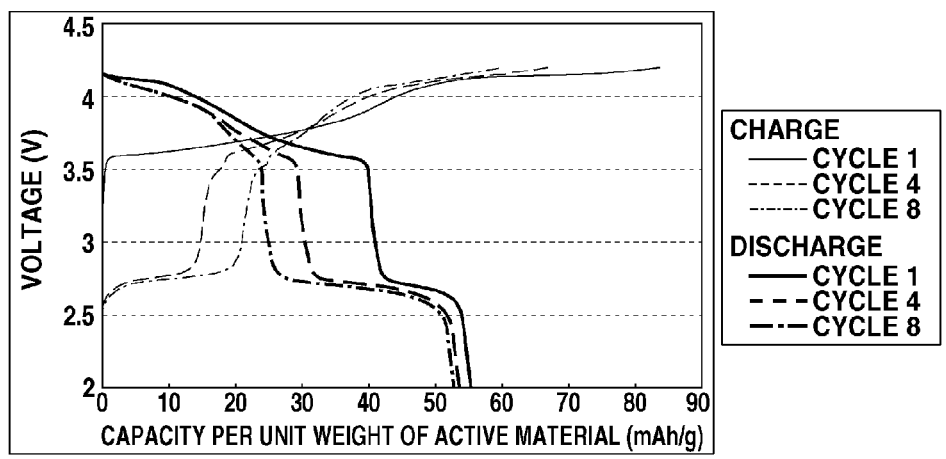
FIG. 23 is a graph showing charge/discharge curves for the first, fourth and eighth cycles of the lithium ion secondary battery fabricated in Comparative Example 3.

In a secondary battery in which P(TEGCz2-PhCHO) was used, the charge-discharge curve gradually changed with the cycle, which made it impossible to obtain a stable charge-discharge performance (FIG. 23). The reason is thought to be that, because the oxidation state of P(TEGCz2-PhCHO) is unstable, structural changes like those shown in above Reaction Scheme A locally arose.

Figure 22:
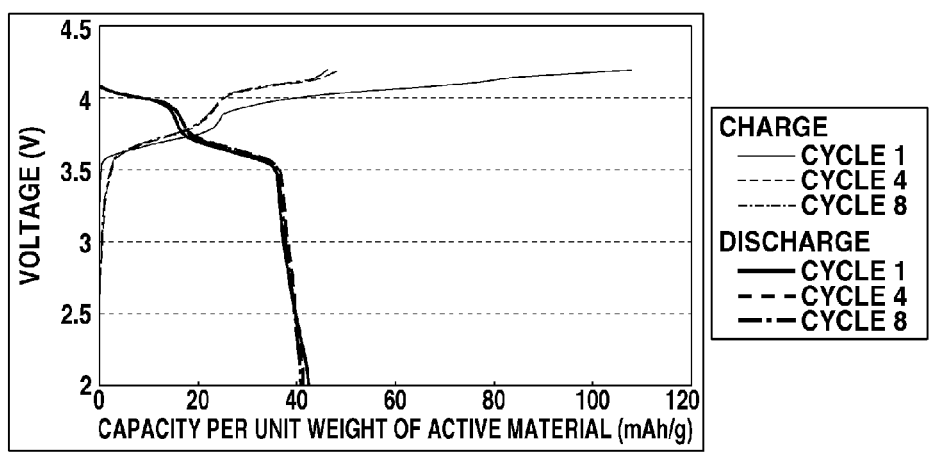
FIG. 22 is a graph showing charge/discharge curves for the first, fourth and eighth cycles of the lithium ion secondary battery fabricated in Example 6.

In a secondary battery in which P(TEGCz2-mDMMB) having a stable oxidation state was used, a stable charge-discharge performance without large changes in the charge-discharge curve even with repeated charging and discharging was exhibited (FIG. 22). In a battery in which P(TEGCz2-PhCHO) was used, the battery voltage decreased with repeated charging and discharging, but in a battery in which P(TEGCz2-mDMMB) was used, the battery voltage was substantially constant even with repeated charging and discharging (FIG. 25).

Hence, given that non-polymeric carbazole derivatives have solubilities which vary greatly depending on the electron state, and that P(TEGCz2-PhCHO) has an unstable oxidation state, these are difficult to use as active materials for lithium ion secondary batteries. By contrast, it was clearly demonstrated that, by using as active materials the carbazole polymers of the invention which are polymers wherein the carbons bonded to carbazole have been made quaternary carbons, lithium ion secondary batteries which maintain a constant battery voltage even with repeated charging and discharging can be fabricated.

The invention claimed is:
  1. A carbazole polymer characterized by comprising recurring units of formula (1)

[Chemical Formula 1]

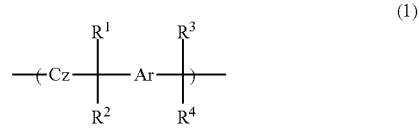

(1)

in formula (1), $R^1$ to $R^4$ are each independently an alkyl group of 1 to 60 carbons, a haloalkyl group of 1 to 60 carbons, a cycloalkyl group of 3 to 60 carbons, a bicycloalkyl group of 4 to 60 carbons, an alkenyl group of 2 to 60 carbons, an alkynyl group of 2 to 60 carbons, an aromatic group of 6 to 60 carbons or a heteroaromatic group of 2 to 60 carbons which alkyl, haloalkyl, cycloalkyl, bicycloalkyl, alkenyl, alkynyl, aromatic and heteroaromatic groups may be substituted with Z;
  Cz is a divalent group that includes the carbazole skeleton of formula (2)

[Chemical Formula 2]

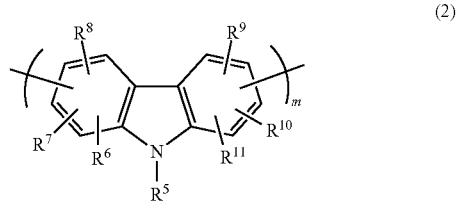

(2)

in formula (2), $R^5$ being a hydrogen atom, an alkyl group of 1 to 60 carbons, a haloalkyl group of 1 to 60 carbons, a cycloalkyl group of 3 to 60 carbons, a bicycloalkyl group of 4 to 60 carbons, an alkenyl group of 2 to 60 carbons, an alkynyl group of 2 to 60 carbons, an aromatic group of 5 to 59 carbons or a heteroaromatic group of 2 to 60 carbons which alkyl, haloalkyl, cycloalkyl, bicycloalkyl, alkenyl, alkynyl, aromatic and heteroaromatic groups may be substituted with Z, and which alkyl groups and haloalkyl groups may include an ether structure, $R^6$ to $R^{11}$ being each independently a hydrogen atom, a halogen atom, a nitro group, a cyano group, an amino group, a hydroxyl group, a thiol group, a phosphate group, a sulfonic acid group, a carboxyl group, an alkoxy group of 1 to 60 carbons, a thioalkoxy group of 1 to 60 carbons, an alkyl group of 1 to 60 carbons, a haloalkyl group of 1 to 60 carbons, a cycloalkyl group of 3 to 60 carbons, a bicycloalkyl group of 4 to 60 carbons, an alkenyl group of 2 to 60 carbons, an alkynyl group of 2 to 60 carbons, an acyl group of 1 to 60 carbons, an aromatic group of 6 to 60 carbons or a heteroaromatic group of 2 to 60 carbons which alkoxy, thioalkoxy, alkyl, haloalkyl, cycloalkyl, bicycloalkyl, alkenyl, alkynyl, acyl, aromatic and heteroaromatic groups may be substituted with Z, and m being an integer from 1 to 10;

Ar is a divalent aromatic ring or heteroaromatic ring which aromatic and heteroaromatic rings may be substituted with Z; and Z is a halogen atom, a nitro group, a cyano group, an amino group, a hydroxyl group, a thiol group, a phosphate group, a sulfonic acid group, a carboxyl group, an alkoxy group of 1 to 60 carbons, a thioalkoxy group of 1 to 60 carbons, an alkyl group of 1 to 60 carbons, a haloalkyl group of 1 to 60 carbons, a cycloalkyl group of 3 to 60 carbons, a bicycloalkyl group of 4 to 60 carbons, an alkenyl group of 2 to 60 carbons, an alkynyl group of 2 to 60 carbons, an acyl group of 1 to 60 carbons, an aromatic group of 6 to 60 carbons or a heteroaromatic group of 2 to 60 carbons.

2. The carbazole polymer according to claim 1, wherein Cz is a divalent group containing a carbazole skeleton of formula (3)

[Chemical Formula 3]

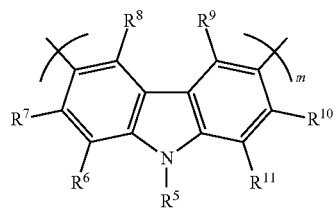

(3)

wherein $R^5$ to $R^{11}$ and m are as defined above.

3. The carbazole polymer according to claim 1, wherein $R^1$ to $R^4$ are each independently an alkyl group of 1 to 10 carbons or a haloalkyl group of 1 to 10 carbons.

4. The carbazole polymer according to claim 3, wherein $R^1$ to $R^4$ are each independently an alkyl group of 1 to 10 carbons.

5. The carbazole polymer according claim 1, wherein $R^5$ is a hydrogen atom, an alkyl group of 1 to 10 carbons, a haloalkyl group of 1 to 10 carbons or a group of formula (4)

[Chemical Formula 4]

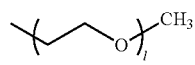

(4)

wherein l is an integer from 1 to 10.

6. The carbazole polymer according to claim 5, wherein $R^5$ is an alkyl group of 1 to 10 carbons or a group of formula (4')

[Chemical Formula 5]

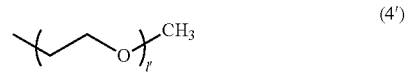

(4')

wherein l' is an integer from 1 to 5.

7. The carbazole polymer according to claim 1, wherein $R^6$ to $R^{11}$ are each independently a hydrogen atom, a halogen atom, an alkyl group of 1 to 10 carbons, a haloalkyl group of 1 to 10 carbons or an alkoxy group of 1 to 10 carbons.

8. The carbazole polymer according to claim 1, wherein Ar is a divalent aromatic ring of any of formulas (5) to (7)

[Chemical Formula 6]

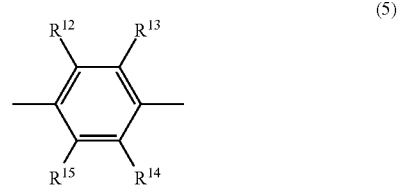

(5)

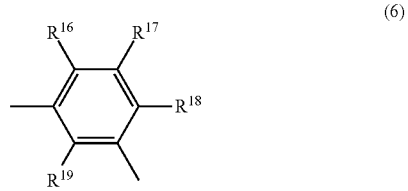

(6)

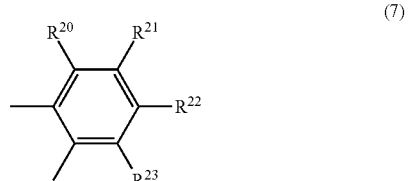

(7)

in formulas (5) to (7), $R^{12}$ to $R^{23}$ are each independently a hydrogen atom, a halogen atom, an alkyl group of 1 to 10 carbons, a haloalkyl group of 1 to 10 carbons or an alkoxy group of 1 to 10 carbons.

9. The carbazole polymer according to claim 1, wherein m is an integer from 1 to 3.

10. The carbazole polymer according to claim 1 of formula (8) or (9)

[Chemical Formula 7]

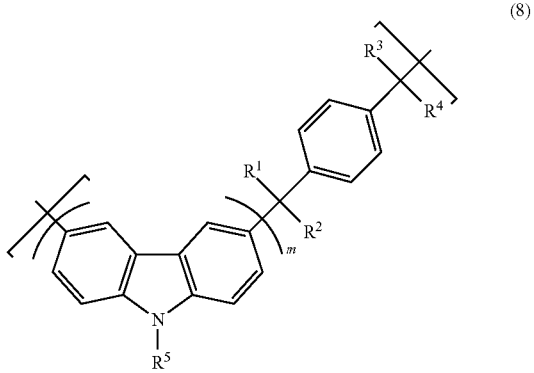

(8)

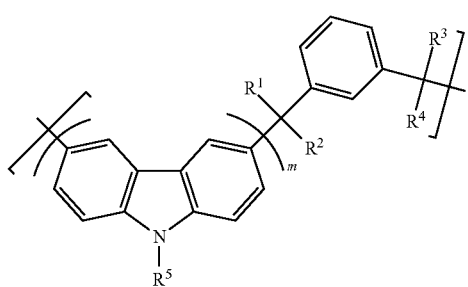

(9)

wherein $R^1$ to $R^5$ and m are as defined above.

11. A method of synthesizing the carbazole polymer according to claim 1, the method being characterized by reacting a carbazole derivative of formula (10) and a bisalcohol compound of formula (11) in the presence of an acid catalyst

[Chemical Formula 8]

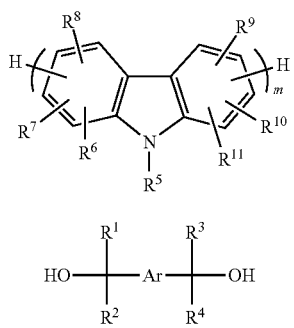

(10)

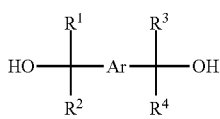

(11)

wherein $R^1$ to $R^{11}$, Ar and m are as defined above.

12. The carbazole polymer synthesis method according to claim 11, wherein the carbazole derivative has formula (12)

[Chemical Formula 9]

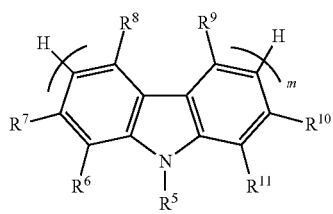

(12)

wherein $R^5$ to $R^{11}$ are as defined above.

13. The carbazole polymer synthesis method according to claim 11, wherein $R^6$ to $R^{11}$ are each independently a hydrogen atom, a halogen atom, an alkyl group of 1 to 10 carbons, a haloalkyl group of 1 to 10 carbons or an alkoxy group of 1 to 10 carbons.

14. The carbazole polymer synthesis method according to claim 11, wherein $R^5$ is a hydrogen atom, an alkyl group of 1 to 10 carbons, a haloalkyl group of 1 to 10 carbons or a group of formula (4)

[Chemical Formula 10]

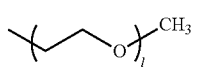

(4)

wherein l is an integer from 1 to 10.

15. The carbazole polymer synthesis method according to claim 11, wherein Ar is a divalent aromatic ring of any of formulas (5) to (7)

[Chemical Formula 11]

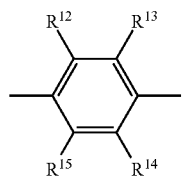

(5)

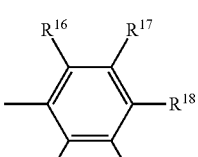

(6)

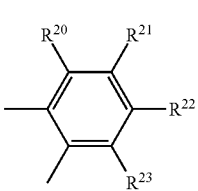

(7)

in formulas (5) to (7), $R^{12}$ to $R^{23}$ are each independently a hydrogen atom, a halogen atom, an alkyl group of 1 to 10 carbons, a haloalkyl group of 1 to 10 carbons or an alkoxy group of 1 to 10 carbons.

16. The carbazole polymer synthesis method according to claim 11, wherein m is an integer from 1 to 3.

17. An electrode active material comprising the carbazole polymer according to claim 1.

18. A composition comprising the carbazole polymer according to claim 1.

19. The composition according to claim 18 which is adapted for use in a secondary battery electrode.

20. An organic electrical storage device which uses the carbazole polymer according to claim 1.

21. An electrode comprising the electrode active material according to claim 17.

22. A secondary battery comprising the electrode according to claim 21.

* * * * *